US012564373B2

(12) United States Patent
McLaughlin et al.

(10) Patent No.: US 12,564,373 B2
(45) Date of Patent: Mar. 3, 2026

(54) SPATIALLY AWARE MEDICAL DEVICE CONFIGURED FOR PERFORMANCE OF INSERTION PATHWAY APPROXIMATION

(71) Applicant: Bard Access Systems, Inc., Salt Lake City, UT (US)

(72) Inventors: William Robert McLaughlin, Bountiful, UT (US); Steffan Sowards, Salt Lake City, UT (US); Anthony K. Misener, Bountiful, UT (US)

(73) Assignee: Bard Access Systems, Inc., Salt Lake City, UT (US)

( * ) Notice: Subject to any disclaimer, the term of this patent is extended or adjusted under 35 U.S.C. 154(b) by 294 days.

(21) Appl. No.: 17/888,359

(22) Filed: Aug. 15, 2022

(65) Prior Publication Data

US 2024/0050061 A1 Feb. 15, 2024

(51) Int. Cl.
| | |
|---|---|
| *A61B 34/20* | (2016.01) |
| *A61B 8/08* | (2006.01) |
| *A61B 8/12* | (2006.01) |

(52) U.S. Cl.
CPC .......... *A61B 8/0891* (2013.01); *A61B 8/0841* (2013.01); *A61B 8/12* (2013.01); *A61B 2034/2063* (2016.02)

(58) Field of Classification Search
CPC ....... A61B 8/0891; A61B 8/0841; A61B 8/12; A61B 8/08; A61B 8/4254; A61B 8/461;
(Continued)

(56) References Cited

U.S. PATENT DOCUMENTS

| | | | |
|---|---|---|---|
| 4,311,138 A | 1/1982 | Sugarman | |
| 4,971,068 A | 11/1990 | Sahi | |
| | (Continued) | | |

FOREIGN PATENT DOCUMENTS

| | | |
|---|---|---|
| AU | 2006201646 A1 | 11/2006 |
| CN | 114129137 B | 9/2022 |
| | (Continued) | |

OTHER PUBLICATIONS

Stolka, P.J., et al., (2014). Needle Guidance Using Handheld Stereo Vision and Projection for Ultrasound-Based Interventions. In: Galland, P., Hata, N., Barillot, C., Hornegger, J., Howe, R. (eds) Medical Image Computing and Computer-Assisted Intervention—MICCAI 2014. MICCAI 2014. (Year: 2014).
(Continued)

*Primary Examiner* — Amal Aly Farag
(74) *Attorney, Agent, or Firm* — Rutan & Tucker LLP

(57) ABSTRACT

An ultrasound-imaging system is disclosed that includes an ultrasound probe and a console. The ultrasound probe includes an array of ultrasonic transducers configured to emit generated ultrasound signals into a patient, receive reflected ultrasound signals, and convert the reflected ultrasound signals into corresponding electrical signals of the ultrasound signals for processing into an ultrasound image, and a component configured to obtain positional-tracking data as the ultrasound probe moves along the patient from a starting position to an end position. The console includes one or more processors and a computer-readable medium storing logic that, when executed, causes operations including: receiving and processing the electrical signals to generate the ultrasound image, receiving the positional-tracking data, determining metrics of a path traveled by the ultrasound probe, and providing insertion recommendations corresponding to a medical device to be inserted into the patient (Continued)

based on the metrics of the path traveled by the ultrasound probe.

18 Claims, 14 Drawing Sheets

(58) Field of Classification Search
CPC .............. A61B 8/085; A61B 17/3403; A61B 2017/3413
See application file for complete search history.

(56) References Cited

U.S. PATENT DOCUMENTS

| | | | |
|---|---|---|---|
| 5,148,809 A | 9/1992 | Biegeleisen-Knight et al. | |
| 5,181,513 A | 1/1993 | Touboul et al. | |
| 5,325,293 A | 6/1994 | Dorne | |
| 5,441,052 A | 8/1995 | Miyajima | |
| 5,549,554 A | 8/1996 | Miraki | |
| 5,573,529 A | 11/1996 | Haak et al. | |
| 5,775,322 A | 7/1998 | Silverstein et al. | |
| 5,879,297 A | 3/1999 | Haynor et al. | |
| 5,908,387 A | 6/1999 | LeFree et al. | |
| 5,967,984 A | 10/1999 | Chu et al. | |
| 5,970,119 A | 10/1999 | Hofmann | |
| 6,004,270 A | 12/1999 | Urbano et al. | |
| 6,019,724 A | 2/2000 | Gronningsaeter et al. | |
| 6,068,599 A | 5/2000 | Saito et al. | |
| 6,074,367 A | 6/2000 | Hubbell | |
| 6,129,668 A | 10/2000 | Haynor et al. | |
| 6,132,379 A | 10/2000 | Patacsil et al. | |
| 6,216,028 B1 | 4/2001 | Haynor et al. | |
| 6,233,476 B1 | 5/2001 | Strommer et al. | |
| 6,245,018 B1 | 6/2001 | Lee | |
| 6,263,230 B1 | 7/2001 | Haynor et al. | |
| 6,375,615 B1 | 4/2002 | Flaherty et al. | |
| 6,436,043 B2 | 8/2002 | Bonnefous | |
| 6,498,942 B1 | 12/2002 | Esenaliev et al. | |
| 6,503,205 B2 | 1/2003 | Manor et al. | |
| 6,508,769 B2 | 1/2003 | Bonnefous | |
| 6,511,458 B2 | 1/2003 | Milo et al. | |
| 6,524,249 B2 | 2/2003 | Moehring et al. | |
| 6,543,642 B1 | 4/2003 | Milliorn | |
| 6,554,771 B1 | 4/2003 | Buil et al. | |
| 6,592,520 B1 | 7/2003 | Peszynski et al. | |
| 6,592,565 B2 | 7/2003 | Twardowski | |
| 6,601,705 B2 | 8/2003 | Molina et al. | |
| 6,612,992 B1 | 9/2003 | Hossack et al. | |
| 6,613,002 B1 | 9/2003 | Clark et al. | |
| 6,623,431 B1 | 9/2003 | Sakuma et al. | |
| 6,641,538 B2 | 11/2003 | Nakaya et al. | |
| 6,647,135 B2 | 11/2003 | Bonnefous | |
| 6,687,386 B1 | 2/2004 | Ito et al. | |
| 6,749,569 B1 | 6/2004 | Pellegretti | |
| 6,754,608 B2 | 6/2004 | Svanerudh et al. | |
| 6,755,789 B2 | 6/2004 | Stringer et al. | |
| 6,840,379 B2 | 1/2005 | Franks-Farah et al. | |
| 6,857,196 B2 | 2/2005 | Dalrymple | |
| 6,979,294 B1 | 12/2005 | Selzer et al. | |
| 7,074,187 B2 | 7/2006 | Selzer et al. | |
| 7,244,234 B2 | 7/2007 | Ridley et al. | |
| 7,359,554 B2 | 4/2008 | Klingensmith et al. | |
| 7,534,209 B2 | 5/2009 | Abend et al. | |
| 7,599,730 B2 | 10/2009 | Hunter et al. | |
| 7,637,870 B2 | 12/2009 | Flaherty et al. | |
| 7,681,579 B2 | 3/2010 | Schwartz | |
| 7,691,061 B2 | 4/2010 | Hirota | |
| 7,699,779 B2 | 4/2010 | Sasaki et al. | |
| 7,720,520 B2 | 5/2010 | Willis | |
| 7,727,153 B2 | 6/2010 | Fritz et al. | |
| 7,734,326 B2 | 6/2010 | Pedain et al. | |
| 7,831,449 B2 | 11/2010 | Ying et al. | |
| 7,905,837 B2 | 3/2011 | Suzuki | |
| 7,925,327 B2 | 4/2011 | Weese | |
| 7,927,278 B2 | 4/2011 | Selzer et al. | |
| 8,014,848 B2 | 9/2011 | Birkenbach et al. | |
| 8,050,523 B2 | 11/2011 | Younge et al. | |
| 8,060,181 B2 | 11/2011 | Rodriguez Ponce et al. | |
| 8,068,581 B2 | 11/2011 | Boese et al. | |
| 8,075,488 B2 | 12/2011 | Burton | |
| 8,090,427 B2 | 1/2012 | Eck et al. | |
| 8,105,239 B2 | 1/2012 | Specht | |
| 8,172,754 B2 | 5/2012 | Watanabe et al. | |
| 8,175,368 B2 | 5/2012 | Sathyanarayana | |
| 8,200,313 B1 | 6/2012 | Rambod et al. | |
| 8,211,023 B2 | 7/2012 | Swan et al. | |
| 8,228,347 B2 | 7/2012 | Beasley et al. | |
| 8,298,147 B2 | 10/2012 | Huennekens et al. | |
| 8,303,505 B2 | 11/2012 | Webler et al. | |
| 8,323,202 B2 | 12/2012 | Roschak et al. | |
| 8,328,727 B2 | 12/2012 | Miele et al. | |
| 8,388,541 B2 | 3/2013 | Messerly et al. | |
| 8,409,103 B2 | 4/2013 | Grunwald et al. | |
| 8,449,465 B2 | 5/2013 | Nair et al. | |
| 8,553,954 B2 | 10/2013 | Saikia | |
| 8,556,815 B2 | 10/2013 | Pelissier et al. | |
| 8,585,600 B2 | 11/2013 | Liu et al. | |
| 8,622,913 B2 | 1/2014 | Dentinger et al. | |
| 8,706,457 B2 | 4/2014 | Hart et al. | |
| 8,727,988 B2 | 5/2014 | Flaherty et al. | |
| 8,734,357 B2 | 5/2014 | Taylor | |
| 8,744,211 B2 | 6/2014 | Owen | |
| 8,754,865 B2 | 6/2014 | Merritt et al. | |
| 8,764,663 B2 | 7/2014 | Smok et al. | |
| 8,781,194 B2 | 7/2014 | Malek et al. | |
| 8,781,555 B2 | 7/2014 | Burnside et al. | |
| 8,790,263 B2 | 7/2014 | Randall et al. | |
| 8,849,382 B2 | 9/2014 | Cox et al. | |
| 8,939,908 B2 | 1/2015 | Suzuki et al. | |
| 8,961,420 B2 | 2/2015 | Zhang | |
| 9,022,940 B2 | 5/2015 | Meier | |
| 9,138,290 B2 | 9/2015 | Hadjicostis | |
| 9,155,517 B2 | 10/2015 | Dunbar et al. | |
| 9,204,858 B2 | 12/2015 | Pelissier et al. | |
| 9,220,477 B2 | 12/2015 | Urabe et al. | |
| 9,257,220 B2 | 2/2016 | Nicholls et al. | |
| 9,295,447 B2 | 3/2016 | Shah | |
| 9,320,493 B2 | 4/2016 | Visveshwara | |
| 9,357,980 B2 | 6/2016 | Toji et al. | |
| 9,364,171 B2 | 6/2016 | Harris et al. | |
| 9,427,207 B2 | 8/2016 | Sheldon et al. | |
| 9,445,780 B2 | 9/2016 | Hossack et al. | |
| 9,456,766 B2 | 10/2016 | Cox et al. | |
| 9,456,804 B2 | 10/2016 | Tamada | |
| 9,459,087 B2 | 10/2016 | Dunbar et al. | |
| 9,468,413 B2 | 10/2016 | Hall et al. | |
| 9,492,097 B2 | 11/2016 | Wilkes et al. | |
| 9,521,961 B2 | 12/2016 | Silverstein et al. | |
| 9,554,716 B2 | 1/2017 | Burnside et al. | |
| 9,582,876 B2 | 2/2017 | Specht | |
| 9,597,008 B2 | 3/2017 | Henkel et al. | |
| 9,610,061 B2 | 4/2017 | Ebbini et al. | |
| 9,636,031 B2 | 5/2017 | Cox | |
| 9,649,037 B2 | 5/2017 | Lowe et al. | |
| 9,649,048 B2 | 5/2017 | Cox et al. | |
| 9,702,969 B2 | 7/2017 | Hope Simpson et al. | |
| 9,715,757 B2 | 7/2017 | Ng et al. | |
| 9,717,415 B2 | 8/2017 | Cohen et al. | |
| 9,731,066 B2 | 8/2017 | Liu et al. | |
| 9,814,433 B2 | 11/2017 | Benishti et al. | |
| 9,814,531 B2 | 11/2017 | Yagi et al. | |
| 9,861,337 B2 | 1/2018 | Patwardhan et al. | |
| 9,895,138 B2 | 2/2018 | Sasaki | |
| 9,913,605 B2 | 3/2018 | Harris et al. | |
| 9,949,720 B2 | 4/2018 | Southard et al. | |
| 10,010,379 B1 | 7/2018 | Gibby et al. | |
| 10,043,272 B2 | 8/2018 | Forzoni et al. | |
| 10,380,919 B2 | 8/2019 | Savitsky et al. | |
| 10,380,920 B2 | 8/2019 | Savitsky et al. | |
| 10,424,225 B2 | 9/2019 | Nataneli et al. | |
| 10,434,278 B2 | 10/2019 | Dunbar et al. | |
| 10,449,330 B2 | 10/2019 | Newman et al. | |
| 10,524,691 B2 | 1/2020 | Newman et al. | |
| 10,636,323 B2 | 4/2020 | Buras et al. | |
| 10,674,935 B2 | 6/2020 | Henkel et al. | |

(56)                References Cited

U.S. PATENT DOCUMENTS

| | | | |
|---|---|---|---|
| 10,751,509 B2 | 8/2020 | Misener | |
| 10,758,155 B2 | 9/2020 | Henkel et al. | |
| 10,765,343 B2 | 9/2020 | Henkel et al. | |
| 10,796,605 B2 | 10/2020 | Buras et al. | |
| 10,818,199 B2 | 10/2020 | Buras et al. | |
| 10,869,727 B2 | 12/2020 | Yanof et al. | |
| 10,896,628 B2 | 1/2021 | Savitsky et al. | |
| 11,011,078 B2 | 5/2021 | Buras et al. | |
| 11,017,694 B2 | 5/2021 | Buras et al. | |
| 11,017,695 B2 | 5/2021 | Buras et al. | |
| 11,062,624 B2 | 7/2021 | Savitsky et al. | |
| 11,120,709 B2 | 9/2021 | Savitsky et al. | |
| 11,311,269 B2 | 4/2022 | Dunbar et al. | |
| 11,315,439 B2 | 4/2022 | Savitsky et al. | |
| 11,495,142 B2 | 11/2022 | Petrinec et al. | |
| 11,600,201 B1 | 3/2023 | Savitsky et al. | |
| 11,676,513 B2 | 6/2023 | Buras et al. | |
| 12,062,297 B2 | 8/2024 | Buras et al. | |
| 12,144,675 B2 | 11/2024 | Durfee | |
| 12,396,656 B2 | 8/2025 | Durfee et al. | |
| 12,414,835 B2 | 9/2025 | Gibby et al. | |
| 2002/0038088 A1 | 3/2002 | Imran et al. | |
| 2002/0148277 A1 | 10/2002 | Umeda | |
| 2003/0028112 A1 | 2/2003 | Paladini et al. | |
| 2003/0047126 A1 | 3/2003 | Tomaschko | |
| 2003/0060714 A1 | 3/2003 | Henderson et al. | |
| 2003/0073900 A1 | 4/2003 | Senarith et al. | |
| 2003/0093001 A1 | 5/2003 | Martikainen | |
| 2003/0106825 A1 | 6/2003 | Molina et al. | |
| 2003/0120154 A1 | 6/2003 | Sauer et al. | |
| 2003/0226868 A1 | 12/2003 | Monden | |
| 2004/0055925 A1 | 3/2004 | Franks-Farah et al. | |
| 2005/0000975 A1 | 1/2005 | Carco et al. | |
| 2005/0049504 A1 | 3/2005 | Lo et al. | |
| 2005/0165299 A1 | 7/2005 | Kressy et al. | |
| 2005/0251030 A1 | 11/2005 | Azar et al. | |
| 2005/0267365 A1 | 12/2005 | Sokulin et al. | |
| 2006/0013523 A1 | 1/2006 | Childlers et al. | |
| 2006/0015039 A1 | 1/2006 | Cassidy et al. | |
| 2006/0020204 A1 | 1/2006 | Serra et al. | |
| 2006/0079781 A1 | 4/2006 | Germond-Rouet et al. | |
| 2006/0184029 A1 | 8/2006 | Haim et al. | |
| 2006/0210130 A1 | 9/2006 | Germond-Rouet et al. | |
| 2007/0043341 A1 | 2/2007 | Anderson et al. | |
| 2007/0049822 A1 | 3/2007 | Bunce et al. | |
| 2007/0073155 A1 | 3/2007 | Park et al. | |
| 2007/0199848 A1 | 8/2007 | Ellswood et al. | |
| 2007/0239120 A1 | 10/2007 | Brock et al. | |
| 2007/0249911 A1 | 10/2007 | Simon | |
| 2008/0021322 A1 | 1/2008 | Stone et al. | |
| 2008/0033293 A1 | 2/2008 | Beasley et al. | |
| 2008/0033759 A1 | 2/2008 | Finlay | |
| 2008/0051657 A1 | 2/2008 | Rold | |
| 2008/0146915 A1 | 6/2008 | McMorrow | |
| 2008/0177186 A1 | 7/2008 | Slater et al. | |
| 2008/0221425 A1 | 9/2008 | Olson et al. | |
| 2008/0255475 A1* | 10/2008 | Kondrosky | A61M 25/09 |
| | | | 600/585 |
| 2008/0294037 A1 | 11/2008 | Richter | |
| 2008/0300491 A1 | 12/2008 | Bonde et al. | |
| 2009/0012399 A1 | 1/2009 | Sunagawa et al. | |
| 2009/0143672 A1 | 6/2009 | Harms et al. | |
| 2009/0143684 A1 | 6/2009 | Cermak et al. | |
| 2009/0156926 A1 | 6/2009 | Messerly et al. | |
| 2009/0306509 A1 | 12/2009 | Pedersen et al. | |
| 2010/0004539 A1 | 1/2010 | Chen et al. | |
| 2010/0020926 A1 | 1/2010 | Boese et al. | |
| 2010/0106015 A1 | 4/2010 | Norris | |
| 2010/0160786 A1 | 6/2010 | Nordgren et al. | |
| 2010/0179428 A1 | 7/2010 | Pedersen et al. | |
| 2010/0211026 A2 | 8/2010 | Sheetz et al. | |
| 2010/0277305 A1 | 11/2010 | Garner et al. | |
| 2010/0286515 A1 | 11/2010 | Gravenstein et al. | |
| 2010/0312121 A1 | 12/2010 | Guan | |
| 2011/0002518 A1 | 1/2011 | Ziv-Ari et al. | |
| 2011/0071404 A1 | 3/2011 | Schmitt et al. | |
| 2011/0166451 A1 | 7/2011 | Blaivas et al. | |
| 2011/0288405 A1 | 11/2011 | Razavi et al. | |
| 2011/0295108 A1 | 12/2011 | Cox et al. | |
| 2011/0313293 A1 | 12/2011 | Lindekugel et al. | |
| 2012/0136242 A1 | 5/2012 | Qi et al. | |
| 2012/0179038 A1 | 7/2012 | Meurer et al. | |
| 2012/0197132 A1 | 8/2012 | O'Connor | |
| 2012/0209121 A1 | 8/2012 | Boudier | |
| 2012/0220865 A1 | 8/2012 | Brown et al. | |
| 2012/0238875 A1 | 9/2012 | Savitsky et al. | |
| 2012/0277576 A1 | 11/2012 | Lui | |
| 2013/0041250 A1 | 2/2013 | Pelissier et al. | |
| 2013/0102889 A1 | 4/2013 | Southard et al. | |
| 2013/0131499 A1 | 5/2013 | Chan et al. | |
| 2013/0131502 A1 | 5/2013 | Blaivas et al. | |
| 2013/0150724 A1 | 6/2013 | Blaivas et al. | |
| 2013/0188832 A1 | 7/2013 | Ma et al. | |
| 2013/0218024 A1 | 8/2013 | Boctor et al. | |
| 2013/0324840 A1 | 12/2013 | Zhongping et al. | |
| 2014/0005530 A1 | 1/2014 | Liu et al. | |
| 2014/0031690 A1 | 1/2014 | Toji et al. | |
| 2014/0036091 A1 | 2/2014 | Zalev et al. | |
| 2014/0073976 A1 | 3/2014 | Fonte et al. | |
| 2014/0100440 A1 | 4/2014 | Cheline et al. | |
| 2014/0155737 A1 | 6/2014 | Manzke et al. | |
| 2014/0180098 A1 | 6/2014 | Flaherty et al. | |
| 2014/0187920 A1* | 7/2014 | Millett | A61B 6/504 |
| | | | 600/424 |
| 2014/0188133 A1 | 7/2014 | Misener | |
| 2014/0188440 A1 | 7/2014 | Donhowe et al. | |
| 2014/0257104 A1 | 9/2014 | Dunbar et al. | |
| 2014/0276059 A1 | 9/2014 | Sheehan | |
| 2014/0276081 A1 | 9/2014 | Tegels | |
| 2014/0276085 A1 | 9/2014 | Miller | |
| 2014/0276690 A1 | 9/2014 | Grace | |
| 2014/0343431 A1 | 11/2014 | Vajinepalli et al. | |
| 2015/0005738 A1 | 1/2015 | Blacker | |
| 2015/0011887 A1 | 1/2015 | Ahn et al. | |
| 2015/0065916 A1 | 3/2015 | Maguire et al. | |
| 2015/0073279 A1 | 3/2015 | Cai et al. | |
| 2015/0112200 A1 | 4/2015 | Oberg et al. | |
| 2015/0157295 A1 | 6/2015 | Liu et al. | |
| 2015/0209113 A1 | 7/2015 | Burkholz et al. | |
| 2015/0209526 A1 | 7/2015 | Matsubara et al. | |
| 2015/0294497 A1 | 10/2015 | Ng et al. | |
| 2015/0297097 A1 | 10/2015 | Matsubara et al. | |
| 2015/0305718 A1* | 10/2015 | Ogasawara | A61B 8/466 |
| | | | 600/440 |
| 2015/0327841 A1 | 11/2015 | Banjanin et al. | |
| 2015/0359991 A1 | 12/2015 | Dunbar et al. | |
| 2016/0029995 A1 | 2/2016 | Navratil et al. | |
| 2016/0029998 A1 | 2/2016 | Brister et al. | |
| 2016/0058420 A1 | 3/2016 | Cinthio et al. | |
| 2016/0100970 A1 | 4/2016 | Brister et al. | |
| 2016/0101263 A1 | 4/2016 | Blumenkranz et al. | |
| 2016/0113699 A1 | 4/2016 | Sverdlik et al. | |
| 2016/0120607 A1 | 5/2016 | Sorotzkin et al. | |
| 2016/0143622 A1 | 5/2016 | Xie et al. | |
| 2016/0157808 A1* | 6/2016 | Merritt | A61B 6/504 |
| | | | 600/407 |
| 2016/0166232 A1 | 6/2016 | Merritt | |
| 2016/0202053 A1 | 7/2016 | Walker et al. | |
| 2016/0213398 A1 | 7/2016 | Liu | |
| 2016/0278743 A1 | 9/2016 | Kawashima | |
| 2016/0278869 A1 | 9/2016 | Grunwald | |
| 2016/0296208 A1 | 10/2016 | Sethuraman et al. | |
| 2016/0374644 A1 | 12/2016 | Mauldin, Jr. et al. | |
| 2017/0056062 A1 | 3/2017 | Buljubasic | |
| 2017/0079548 A1 | 3/2017 | Silverstein et al. | |
| 2017/0086785 A1 | 3/2017 | Bjaerum | |
| 2017/0100092 A1 | 4/2017 | Kruse et al. | |
| 2017/0164923 A1 | 6/2017 | Matsumoto | |
| 2017/0172424 A1 | 6/2017 | Eggers et al. | |
| 2017/0188839 A1 | 7/2017 | Tashiro | |
| 2017/0196535 A1 | 7/2017 | Arai et al. | |
| 2017/0215842 A1 | 8/2017 | Ryu et al. | |
| 2017/0259013 A1 | 9/2017 | Boyden et al. | |
| 2017/0265840 A1 | 9/2017 | Bharat et al. | |

(56) References Cited

U.S. PATENT DOCUMENTS

| | | |
|---|---|---|
| 2017/0303894 A1 | 10/2017 | Scully |
| 2017/0367678 A1 | 12/2017 | Sirtori et al. |
| 2018/0015256 A1 | 1/2018 | Southard et al. |
| 2018/0116723 A1 | 5/2018 | Hettrick et al. |
| 2018/0125450 A1 | 5/2018 | Blackbourne et al. |
| 2018/0161502 A1 | 6/2018 | Nanan et al. |
| 2018/0199914 A1 | 7/2018 | Ramachandran et al. |
| 2018/0214119 A1 | 8/2018 | Mehrmohammadi et al. |
| 2018/0220993 A1 | 8/2018 | Poland |
| 2018/0225993 A1 | 8/2018 | Buras et al. |
| 2018/0228465 A1 | 8/2018 | Southard et al. |
| 2018/0235576 A1 | 8/2018 | Brannan |
| 2018/0250078 A1 | 9/2018 | Shochat et al. |
| 2018/0272108 A1 | 9/2018 | Padilla et al. |
| 2018/0279996 A1 | 10/2018 | Cox et al. |
| 2018/0286287 A1 | 10/2018 | Razzaque |
| 2018/0310955 A1 | 11/2018 | Lindekugel et al. |
| 2018/0317881 A1 | 11/2018 | Astigarraga et al. |
| 2018/0366035 A1 | 12/2018 | Dunbar et al. |
| 2019/0060014 A1 | 2/2019 | Hazelton et al. |
| 2019/0069923 A1 | 3/2019 | Wang |
| 2019/0076121 A1 | 3/2019 | Southard et al. |
| 2019/0088019 A1 | 3/2019 | Prevrhal et al. |
| 2019/0105017 A1 | 4/2019 | Hastings |
| 2019/0117190 A1 | 4/2019 | Djajadiningrat et al. |
| 2019/0167148 A1 | 6/2019 | Durfee et al. |
| 2019/0223757 A1 | 7/2019 | Durfee |
| 2019/0223958 A1 | 7/2019 | Kohli et al. |
| 2019/0239850 A1 | 8/2019 | Dalvin et al. |
| 2019/0282324 A1 | 9/2019 | Freeman et al. |
| 2019/0298457 A1 | 10/2019 | Bharat |
| 2019/0307419 A1 | 10/2019 | Durfee |
| 2019/0307516 A1 | 10/2019 | Schotzko et al. |
| 2019/0339525 A1 | 11/2019 | Yanof et al. |
| 2019/0355278 A1 | 11/2019 | Sainsbury et al. |
| 2019/0365348 A1 | 12/2019 | Toume et al. |
| 2020/0041261 A1 | 2/2020 | Bernstein et al. |
| 2020/0069285 A1 | 3/2020 | Annangi et al. |
| 2020/0069929 A1 | 3/2020 | Mason et al. |
| 2020/0113540 A1 | 4/2020 | Gijsbers et al. |
| 2020/0129136 A1 | 4/2020 | Harding et al. |
| 2020/0188028 A1 | 6/2020 | Feiner et al. |
| 2020/0230391 A1 | 7/2020 | Burkholz et al. |
| 2020/0305927 A1 | 10/2020 | Grim et al. |
| 2020/0367860 A1* | 11/2020 | Rouet ................... A61B 8/483 |
| 2021/0007710 A1 | 1/2021 | Douglas |
| 2021/0045716 A1 | 2/2021 | Shiran et al. |
| 2021/0161612 A1 | 6/2021 | Black et al. |
| 2021/0166583 A1 | 6/2021 | Buras et al. |
| 2021/0307838 A1 | 10/2021 | Xia et al. |
| 2021/0327303 A1 | 10/2021 | Buras et al. |
| 2021/0353255 A1 | 11/2021 | Schneider et al. |
| 2021/0402144 A1 | 12/2021 | Messerly |
| 2022/0022969 A1 | 1/2022 | Misener |
| 2022/0031965 A1 | 2/2022 | Durfee |
| 2022/0039685 A1 | 2/2022 | Misener et al. |
| 2022/0039777 A1 | 2/2022 | Durfee |
| 2022/0096797 A1 | 3/2022 | Prince |
| 2022/0104886 A1 | 4/2022 | Blanchard et al. |
| 2022/0117582 A1 | 4/2022 | McLaughlin et al. |
| 2022/0160434 A1 | 5/2022 | Messerly et al. |
| 2022/0168050 A1 | 6/2022 | Sowards et al. |
| 2022/0172354 A1 | 6/2022 | Misener et al. |
| 2022/0211442 A1 | 7/2022 | McLaughlin et al. |
| 2022/0354462 A1 | 11/2022 | Southworth et al. |
| 2022/0381630 A1 | 12/2022 | Sowards et al. |
| 2022/0401157 A1 | 12/2022 | Sowards et al. |
| 2023/0053189 A1 | 2/2023 | Geric et al. |
| 2023/0113291 A1 | 4/2023 | de Wild et al. |
| 2023/0240643 A1 | 8/2023 | Cermak et al. |
| 2023/0389893 A1 | 12/2023 | Misener et al. |
| 2024/0008929 A1 | 1/2024 | Misener et al. |
| 2024/0058074 A1 | 2/2024 | Misener |
| 2024/0062678 A1 | 2/2024 | Sowards et al. |
| 2025/0000488 A1 | 1/2025 | Misener et al. |
| 2025/0032152 A1 | 1/2025 | Miller et al. |
| 2025/0057604 A1 | 2/2025 | Blanchard et al. |
| 2025/0064425 A1 | 2/2025 | Durfee |
| 2025/0143804 A1 | 5/2025 | Misener |
| 2025/0176942 A1 | 6/2025 | McLaughlin et al. |
| 2025/0339174 A1 | 11/2025 | Durfee et al. |

FOREIGN PATENT DOCUMENTS

| | | |
|---|---|---|
| EP | 0933063 A1 | 8/1999 |
| EP | 1504713 A1 | 2/2005 |
| EP | 1591074 B1 | 5/2008 |
| EP | 3181083 A1 | 6/2017 |
| EP | 3530221 A1 | 8/2019 |
| JP | 2000271136 A | 10/2000 |
| JP | 2014150928 A | 8/2014 |
| JP | 2018175547 A | 11/2018 |
| KR | 20180070878 A | 6/2018 |
| KR | 20190013133 A | 2/2019 |
| KR | 20220141308 A | 10/2022 |
| WO | 2013059714 A1 | 4/2013 |
| WO | 2014/115150 A1 | 7/2014 |
| WO | 2014174305 A2 | 10/2014 |
| WO | 2015/017270 A1 | 2/2015 |
| WO | 2017096487 A1 | 6/2017 |
| WO | 2017214428 A1 | 12/2017 |
| WO | 2018/026878 A1 | 2/2018 |
| WO | 2018134726 A1 | 7/2018 |
| WO | 2018206473 A1 | 11/2018 |
| WO | 2019/232451 A1 | 12/2019 |
| WO | 2020/002620 A1 | 1/2020 |
| WO | 2020/016018 A1 | 1/2020 |
| WO | 2019/232454 A9 | 2/2020 |
| WO | 2020/044769 A1 | 3/2020 |
| WO | 2020102665 A1 | 5/2020 |
| WO | 2020/186198 A1 | 9/2020 |
| WO | 2022/031762 A1 | 2/2022 |
| WO | 2022/072727 A2 | 4/2022 |
| WO | 2022/081904 A1 | 4/2022 |
| WO | 2022-203713 A2 | 9/2022 |
| WO | 2022263763 A1 | 12/2022 |
| WO | 2023235435 A1 | 12/2023 |
| WO | 2024010940 A1 | 1/2024 |
| WO | 2024039608 A1 | 2/2024 |
| WO | 2024039719 A1 | 2/2024 |
| WO | 2025024821 A1 | 1/2025 |

OTHER PUBLICATIONS

U.S. Appl. No. 17/491,308, filed Sep. 30, 2021 Non-Final Office Action dated Jun. 5, 2023.

U.S. Appl. No. 17/501,909, filed Oct. 14, 2021 Non-Final Office Action dated Jun. 6, 2023.

U.S. Appl. No. 17/832,389, filed Jun. 3, 2022 Restriction Requirement dated Jul. 13, 2023.

PCT/US2021/050973 filed Sep. 17, 2021 International Search Report and Written Opinion dated Nov. 7, 2022.

U.S. Appl. No. 17/380,767, filed Jul. 20, 2021 Restriction Requirement dated Dec. 15, 2022.

U.S. Appl. No. 17/393,283, filed Aug. 3, 2021 Restriction Requirement dated Jan. 12, 2023.

U.S. Appl. No. 17/397,486, filed Aug. 9, 2021 Non-Final Office Action dated Jan. 23, 2023.

U.S. Appl. No. 17/501,909, filed Oct. 14, 2021 Restriction Requirement dated Feb. 1, 2023.

EZono, eZSimulator, https://www.ezono.com/en/ezsimulator/, last accessed Sep. 13, 2022.

Ikhsan Mohammad et al: "Assistive technology for ultrasound-guided central venous catheter placement", Journal of Medical Ultrasonics, Japan Society of Ultrasonics in Medicine, Tokyo, JP, vol. 45, No. 1, Apr. 19, 2017, pp. 41-57, XPO36387340, ISSN: 1346-4523, DOI: 10.1007/S10396-017-0789-2 [retrieved on Ape. 19, 2017].

Lu Zhenyu et al "Recent advances in 5 robot-assisted echography combining perception control and cognition." Cognitive Computation and Systems the Institution of Engineering and Technology,

(56) References Cited

OTHER PUBLICATIONS

Michael Faraday House, Six Hills Way, Stevenage Herts. SG1 2AY UK vol. 2 No. 3 Sep. 2, 2020 (Sep. 2, 2020).

Pagoulatos, N. et al. "New spatial localizer based on fiber optics with applications in 3D ultrasound imaging" Proceeding of Spie, vol. 3976 (Apr. 18, 2000; Apr. 18, 2000).

PCT/US2021/042369 filed Jul. 20, 2021 International Search Report and Written Opinion dated Oct. 25, 2021.

PCT/US2021/044419 filed Aug. 3, 2021 International Search Report and Written Opinion dated Nov. 19, 2021.

PCT/US2021/045218 filed Aug. 9, 2021 International Search Report and Written Opinion dated Nov. 23, 2021.

PCT/US2021/053018 filed Sep. 30, 2021 International Search Report and Written Opinion dated May 3, 2022.

PCT/US2021/055076 filed Oct. 14, 2021 International Search Report and Written Opinion dated Mar. 25, 2022.

Sebastian Vogt: "Real-Time Augmented Reality for Image-Guided Interventions", Oct. 5, 2009, XPO55354720, Retrieved from the Internet: URL: https://opus4.kobv.de/opus4-fau/frontdoor/deliver/index/docId/1235/file/SebastianVogtDissertation.pdf.

Sonosim, https://sonosim.com/ultrasound-simulation/? last accessed Sep. 13, 2022.

U.S. Appl. No. 17/397,486, filed Aug. 9, 2021 Restriction Requirement dated Aug. 12, 2022.

William F Garrett et al: "Real-time incremental visualization of dynamic ultrasound vols. using parallel BSP trees", Visualization '96. Proceedings, IEEE, NE, Oct. 27, 1996, pp. 235-ff, XPO58399771, ISBN: 978-0-89791-864-0 abstract, figures 1-7, pp. 236-240.

U.S. Appl. No. 17/393,283, filed Aug. 3, 2021 Notice of Allowance dated Sep. 18, 2024.

U.S. Appl. No. 17/397,486, filed Aug. 9, 2021 Notice of Allowance dated Jul. 10, 2024.

U.S. Appl. No. 17/478,754, filed Sep. 17, 2021 Non-Final Office Action dated Jul. 1, 2024.

U.S. Appl. No. 17/491,308, filed Sep. 30, 2021 Notice of Allowance dated Jun. 27, 2024.

U.S. Appl. No. 17/501,909, filed Oct. 14, 2021 Final Office Action dated Aug. 5, 2024.

U.S. Appl. No. 17/501,909, filed Oct. 14, 2021 Notice of Allowance dated Sep. 25, 2024.

U.S. Appl. No. 17/832,389, filed Jun. 3, 2022 Notice of Allowance dated May 15, 2024.

U.S. Appl. No. 17/861,031, filed Jul. 8, 2022 Advisory Action dated Jun. 7, 2024.

U.S. Appl. No. 17/861,031, filed Jul. 8, 2022 Notice of Allowance dated Jul. 3, 2024.

U.S. Appl. No. 18/385,101, filed Oct. 30, 2023 Notice of Allowance dated Aug. 20, 2024.

U.S. Appl. No. 17/393,283, filed Aug. 3, 2021 Non-Final Office Action dated Feb. 29, 2024.

U.S. Appl. No. 17/397,486, filed Aug. 9, 2021 Non-Final Office Action dated Mar. 1, 2024.

U.S. Appl. No. 17/491,308, filed Sep. 30, 2021 Non-Final Office Action dated Mar. 22, 2024.

U.S. Appl. No. 17/501,909, filed Oct. 14, 2021 Advisory Action dated Jan. 24, 2024.

U.S. Appl. No. 17/501,909, filed Oct. 14, 2021 Non-Final Office Action dated Mar. 21, 2024.

U.S. Appl. No. 17/832,389, filed Jun. 3, 2022 Advisory Action dated Apr. 4, 2024.

U.S. Appl. No. 17/832,389, filed Jun. 3, 2022 Final Office Action dated Jan. 25, 2024.

U.S. Appl. No. 17/861,031, filed Jul. 8, 2022 Final Office Action dated Mar. 15, 2024.

PCT/US2023/024067 filed May 31, 2023 International Search Report and Written Opinion dated Sep. 15, 2023.

PCT/US2023/027147 filed Jul. 7, 2023 International Search Report and Written Opinion dated Oct. 2, 2023.

State, A., et al. (Aug. 1996). Technologies for augmented reality systems: Realizing ultrasound-guided needle biopsies. In Proceedings of the 23rd annual conference on computer graphics and interactive techniques (pp. 439-446) (Year: 1996).

U.S. Appl. No. 17/380,767, filed Jul. 20, 2021 Notice of Allowance dated Aug. 31, 2023.

U.S. Appl. No. 17/393,283, filed Aug. 3, 2021 Final Office Action dated Oct. 16, 2023.

U.S. Appl. No. 17/397,486, filed Aug. 9, 2021 Advisory Action dated Oct. 5, 2023.

U.S. Appl. No. 17/397,486, filed Aug. 9, 2021 Final Office Action dated Aug. 4, 2023.

U.S. Appl. No. 17/491,308, filed Sep. 30, 2021 Board Decison dated Oct. 25, 2023.

U.S. Appl. No. 17/491,308, filed Sep. 30, 2021 Final Office Action dated Aug. 29, 2023.

U.S. Appl. No. 17/832,389, filed Jun. 3, 2022 Non-Final Office Action dated Oct. 6, 2023.

U.S. Appl. No. 17/861,031, filed Jul. 8, 2022 Non-Final Office Action dated Sep. 14, 2023.

PCT/US2023/030160 filed Aug. 14, 2023 International Search Report and Written Opinion dated Oct. 23, 2023.

PCT/US2023/030347 filed Aug. 16, 2023 International Search Report and Written Opinion dated Nov. 6, 2023.

Practical guide for safe central venous catheterization and management 2017 Journal of Anesthesia vol. 34 published online Nov. 30, 2019 pp. 167-186.

U.S. Appl. No. 17/393,283, filed Aug. 3, 2021 Advisory Action dated Jan. 19, 2024.

U.S. Appl. No. 17/478,754, filed Sep. 17, 2021 Restriction Requirement dated Jan. 22, 2024.

U.S. Appl. No. 17/501,909, filed Oct. 14, 2021 Final Office Action dated Nov. 21, 2023.

U.S. Appl. No. 17/380,767, filed Jul. 20, 2021 Non-Final Office Action dated Mar. 6, 2023.

U.S. Appl. No. 17/393,283, filed Aug. 3, 2021 Non-Final Office Action dated Mar. 31, 2023.

U.S. Appl. No. 17/491,308, filed Sep. 30, 2021 Restriction Requirement dated Feb. 27, 2023.

PCT/US2024/039922 filed Jul. 26, 2024 International Search Report and Written Opinion dated Jan. 9, 2025.

U.S. Appl. No. 17/478,754, filed Sep. 17, 2021 Non-Final Office Action dated Dec. 30, 2024.

Manuel Birlo et al: "Utility of Optical See-Through Head Mounted Displays in Augmented Reality-Assisted Surgery: A systematic review", arxiv.org, Cornell University Library, 201 Olin Library Cornell University Ithaca, NY 14853, Feb. 8, 2022 (Feb. 8, 2022), XP091157128, DOI: 10.1016/J.MEDIA.2022.102361 Section 8.5, section 8.2.

PCT/US2025/027390 filed May 1, 2025 International Search Report and Written Opinion dated Jul. 29, 2025.

U.S. Appl. No. 17/478,754, filed Sep. 17, 2021 Advisory Action dated Jun. 24, 2025.

U.S. Appl. No. 17/478,754, filed Sep. 17, 2021 Final Office Action dated Apr. 11, 2025.

U.S. Appl. No. 17/478,754, filed Sep. 17, 2021 Notice of Allowance dated Aug. 14, 2025.

U.S. Appl. No. 17/890,148, filed Aug. 17, 2022 Non-Final Office Action dated Sep. 9, 2025.

U.S. Appl. No. 18/652,728, filed May 1, 2024 Non-Final Office Action dated Oct. 1, 2025.

U.S. Appl. No. 18/885,090, filed Sep. 13, 2024 Non-Final Office Action dated Sep. 29, 2025.

U.S. Appl. No. 18/936,364, filed Nov. 4, 2024 Non-Final Office Action dated Feb. 5, 2025.

* cited by examiner

SPATIALLY AWARE MEDICAL DEVICE CONFIGURED FOR PERFORMANCE OF INSERTION PATHWAY APPROXIMATION

BACKGROUND

Ultrasound imaging is a widely accepted tool for guiding interventional instruments such as needles, catheters, stylets, and guidewires to targets such as blood vessels or organs in the human body. However, current ultrasound imaging systems and accepted procedures generally lack accurate determination or approximation of insertion pathway measurements such as a length of an anticipated insertion pathway from an insertion site to the target placement position within the vasculature. For instance, the current, accepted practice is to utilize a paper tape measurer to measure a distance from the insertion site to an external position on a patient body believed to be above the target placement position. However, such a practice is severely outdated given today's advances in medical instruments.

Disclosed herein are systems including ultrasound imaging probes having integrated therein components for obtaining positional-tracking data of the probe during a pre-scan procedure (a mapping procedure) and logic for analyzing the positional-tracking data to determine a starting position for the probe during a scanning procedure, which may accompany the insertion of needle and/or medical device into a patient. Additionally, the positional-tracking data obtained during the pre-scan procedure may enable the logic to generate a visualization of an intended insertion pathway through the vasculature of the patient (e.g., generate a visual of a set of vessels through which a medical device will travel prior to placement at a target location). Additionally, disclosed herein are methods of use of such ultrasound imaging probes.

SUMMARY

Disclosed herein is an ultrasound-imaging system including, in some embodiments, an ultrasound probe including (i) an array of ultrasonic transducers, wherein activated ultrasonic transducers of the array of ultrasonic transducers configured to emit generated ultrasound signals into a patient, receive reflected ultrasound signals from the patient, and convert the reflected ultrasound signals into corresponding electrical signals of the ultrasound signals for processing into an ultrasound image, and (ii) a component configured to obtain positional-tracking data as the ultrasound probe is moved along a patient body from a starting position to an end position. The ultrasound-imaging system further includes a console configured to communicate with the ultrasound probe. The console includes one or more processors and a non-transitory computer-readable medium having stored thereon logic, when executed by the one or more processors, causes operations including: receiving and processing the electrical signals to generate the ultrasound image, receiving the positional-tracking data, determining metrics of a path traveled by the ultrasound probe, and providing insertion recommendations corresponding to a medical device to be inserted into the patient based on the metrics of the path traveled by the ultrasound probe.

In some embodiments, obtaining the positional-tracking data is a pre-scan procedure performed prior to sanitizing an insertion site. In some embodiments, the metrics of the path traveled by the ultrasound probe include a distance traveled from the starting position to the end position. In other embodiments, the component configured to obtain the positional-tracking data is an inertial measurement unit. In further embodiments, the component configured to obtain the positional-tracking data is a multi-core optical fiber that is configured in a predetermined geometry within the probe.

In yet other embodiments, the component configured to obtain the positional-tracking data is a magnetic sensor, and the ultrasound-imaging system further comprises: one or more magnetic targets, wherein the magnetic sensor is configured to detect variations in a strength of magnetic fields generated by the one or more magnetic targets as the ultrasound probe moves from the starting position to the end position.

The ultrasound-imaging system may further comprise an alternative reality device communicatively coupled to the console and configured to display an alternative reality display of the ultrasound image as the ultrasound probe moves from the starting position to the end position. In some embodiments, at least one of the console or the ultrasound probe are configured to provide feedback when the ultrasound probe is returned to the starting position following sanitization of the insertion site. The feedback may be any of audible feedback, haptic feedback, or visual feedback.

In some embodiments, the logic, when executed by the one or more processors, causes further operations including: receiving user input providing refinement data corresponding to an aspect of the positional-tracking data or the ultrasound image, wherein the refinement data is any of a depth of an imaged vessel with the ultrasound image or patient specific information.

Additionally, disclosed herein is non-transitory, computer-readable medium having stored thereon logic that, when executed by one or more processors, cause operations including a method of utilizing an ultrasound-imaging system including receiving and processing the electrical signals to generate the ultrasound image, receiving the positional-tracking data, determining metrics of a path traveled by the ultrasound probe, and providing insertion recommendations corresponding to a medical device to be inserted into the patient based on the metrics of the path traveled by the ultrasound probe.

These and other features of the concepts provided herein will become more apparent to those of skill in the art in view of the accompanying drawings and following description, which describe particular embodiments of such concepts in greater detail.

BRIEF DESCRIPTION OF THE DRAWINGS

One or more embodiments of the present disclosure are illustrated by way of example and not limitation in the figures of the accompanying drawings, in which like references indicate similar elements.

DETAILED DESCRIPTION

Figure 1:
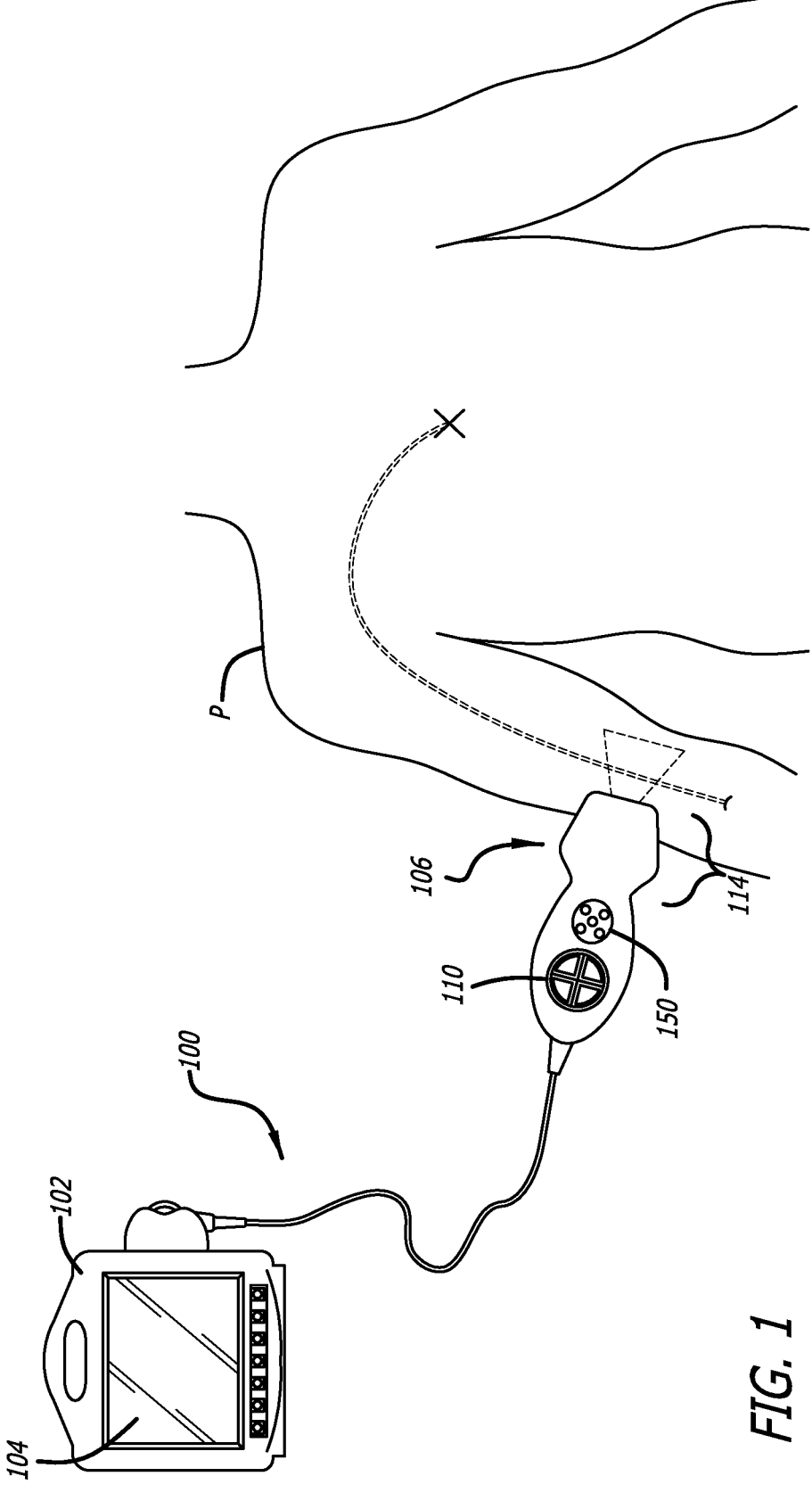
FIG. 1 illustrates an ultrasound-imaging system and a patient in accordance with some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

In this description, references to "an embodiment," "one embodiment" or the like, mean that the particular feature, function, structure or characteristic being described is included in at least one embodiment of the technique introduced herein. Occurrences of such phrases in this specification do not necessarily all refer to the same embodiment. On the other hand, the embodiments referred to also are not necessarily mutually exclusive.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal-end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal-end portion, or the proximal length of the catheter can include the proximal end of the catheter; however, the proximal portion, the proximal-end portion, or the proximal length of the catheter need not include the proximal end of the catheter. That is, unless context suggests otherwise, the proximal portion, the proximal-end portion, or the proximal length of the catheter is not a terminal portion or terminal length of the catheter.

With respect to "distal," a "distal portion" or a "distal-end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal-end portion, or the distal length of the catheter can include the distal end of the catheter; however, the distal portion, the distal-end portion, or the distal length of the catheter need not include the distal end of the catheter. That is, unless context suggests otherwise, the distal portion, the distal-end portion, or the distal length of the catheter is not a terminal portion or terminal length of the catheter.

Unless defined otherwise, all technical and scientific terms used herein have the same meaning as commonly understood by those of ordinary skill in the art.

As set forth above, ultrasound-imaging systems and methods thereof are needed that can dynamically adjust the image plane to facilitate guiding interventional instruments to targets in at least the human body. Disclosed herein are dynamically adjusting ultrasound-imaging systems and methods thereof.

Figure 2:
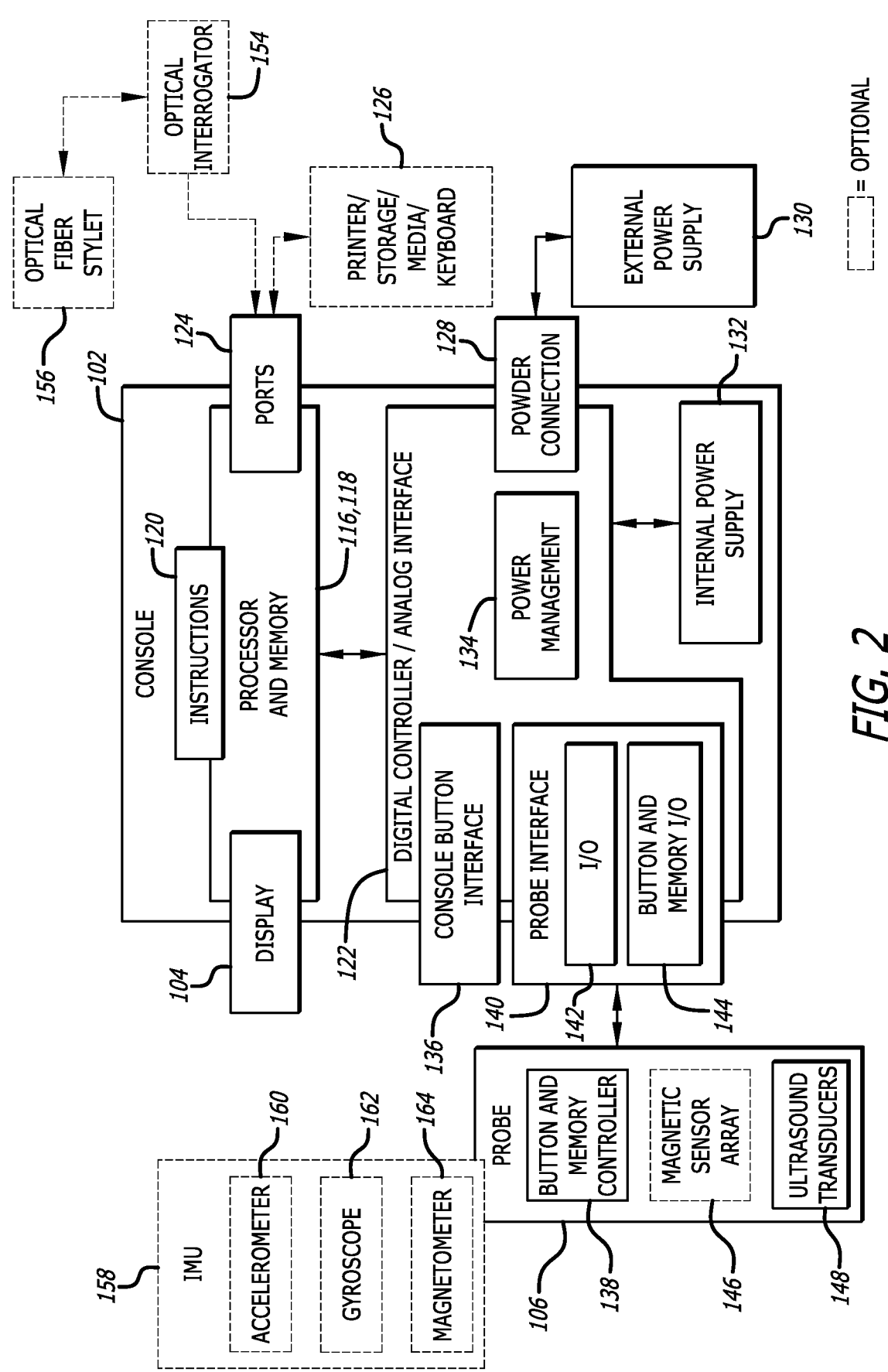
FIG. 2 illustrates a block diagram of a console of the ultrasound-imaging system of FIG. 1 in accordance with some embodiments.
Figure 3:
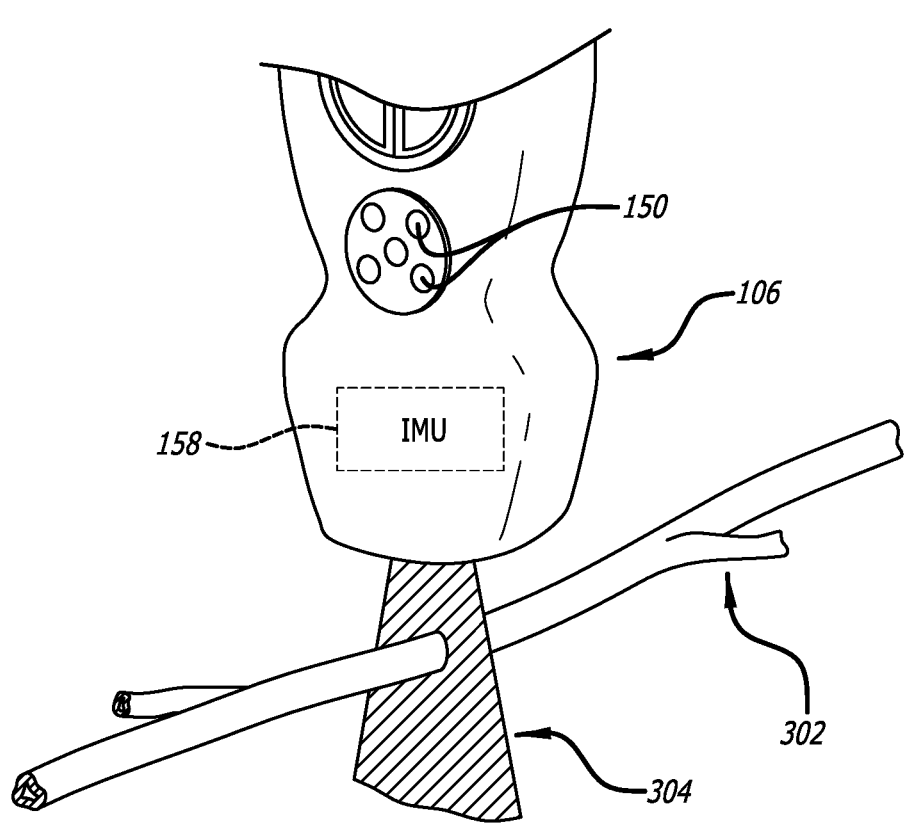
FIG. 3 illustrates a first embodiment of an ultrasound probe that may be included in the ultrasound-imaging system of FIG. 1 in accordance with some embodiments.

Referring now to FIG. 1, an illustration of an ultrasound-imaging system 100, a needle 112, and a patient P is shown in accordance with some embodiments. FIG. 2 illustrates a block diagram of the ultrasound-imaging system 100 in accordance with some embodiments. FIG. 3 illustrates an ultrasound probe 106 of the ultrasound-imaging system 100 imaging a blood vessel of the patient P prior to accessing the blood vessel in accordance with some embodiments.

As shown, the ultrasound-imaging system 100 includes a console 102, the display screen 104, and the ultrasound probe 106. The ultrasound-imaging system 100 is useful for imaging a target such as a blood vessel or an organ within a body of the patient P prior to a percutaneous puncture with the needle 112 for inserting the needle 112 or another medical device into the target and accessing the target. Indeed, the ultrasound-imaging system 100 is shown in FIG. 1 in a general relationship to the patient P during an ultrasound-based medical procedure to place a catheter 108 into the vasculature of the patient P through a skin insertion site S created by a percutaneous puncture with the needle 112. It should be appreciated that the ultrasound-imaging system 100 can be useful in a variety of ultrasound-based medical procedures other than catheterization. For example, the percutaneous puncture with the needle 112 can be performed to biopsy tissue of an organ of the patient P.

The console 102 houses a variety of components of the ultrasound-imaging system 100, and it is appreciated the console 102 can take any of a variety of forms. A processor 116 and memory 118 such as random-access memory ("RAM") or non-volatile memory (e.g., electrically erasable programmable read-only memory ("EEPROM")) is included in the console 102 for controlling functions of the ultrasound-imaging system 100, as well as executing various logic operations or algorithms during operation of the ultrasound-imaging system 100 in accordance with executable logic 120 therefor stored in the memory 118 for execution by the processor 116. For example, the console 102 is configured to instantiate by way of the logic 120 one or more processes for dynamically adjusting a distance of activated ultrasonic transducers 149 from a predefined target (e.g., blood vessel) or area, an orientation of the activated ultrasonic transducers 149 to the predefined target or area, or both the distance and the orientation of the activated ultrasonic transducers 149 with respect to the predefined target or area, as well as process electrical signals from the ultrasound probe 106 into ultrasound images. Dynamically adjusting the activated ultrasonic transducers 149 uses ultrasound-imaging data, magnetic-field data, shape-sensing data, or a combination thereof received by the console 102 for activating certain ultrasonic transducers of a 2-D array of the ultrasonic transducers 148 or moving those already activated in a linear array of the ultrasonic transducers 148. A digital controller/analog interface 122 is also included with the console 102 and is in communication with both the processor 116 and other system components to govern interfacing between the ultrasound probe 106 and other system components set forth herein.

The ultrasound-imaging system 100 further includes ports 124 for connection with additional components such as optional components 126 including a printer, storage media, keyboard, etc. The ports 124 can be universal serial bus ("USB") ports, though other types of ports can be used for this connection, or any other connections shown or described herein. A power connection 128 is included with the console 102 to enable operable connection to an external power supply 130. An internal power supply 132 (e.g., a battery) can also be employed either with or exclusive of the external power supply 130. Power management circuitry 134 is included with the digital controller/analog interface 122 of the console 102 to regulate power use and distribution.

The display screen 104 is integrated into the console 102 to provide a GUI and display information for a clinician during such as one-or-more ultrasound images of the target or the patient P attained by the ultrasound probe 106. In addition, the ultrasound-imaging system 100 enables the distance and orientation of a magnetized medical device such as the needle 112 to be superimposed in real-time atop an ultrasound image of the target, thus enabling a clinician to accurately guide the magnetized medical device to the intended target. Notwithstanding the foregoing, the display screen 104 can alternatively be separate from the console 102 and communicatively coupled thereto. A console button interface 136 and control buttons 110 (see FIG. 1) included on the ultrasound probe 106 can be used to immediately call up a desired mode to the display screen 104 by the clinician for assistance in an ultrasound-based medical procedure. In some embodiments, the display screen 104 is an LCD device.

The ultrasound probe 106 is employed in connection with ultrasound-based visualization of a target such as a blood vessel (see FIG. 3) in preparation for inserting the needle 112 or another medical device into the target. Such visualization gives real-time ultrasound guidance and assists in reducing complications typically associated with such insertion, including inadvertent arterial puncture, hematoma, pneumothorax, etc. As described in more detail below, the ultrasound probe 106 is configured to provide to the console 102 electrical signals corresponding to both the ultrasound-imaging data, the magnetic-field data, the shape-sensing data, or a combination thereof for the real-time ultrasound guidance.

Optionally, a stand-alone optical interrogator 154 can be communicatively coupled to the console 102 by way of one of the ports 124. Alternatively, the console 102 can include an integrated optical interrogator integrated into the console 102. Such an optical interrogator is configured to emit input optical signals into a companion optical-fiber stylet 156 for shape sensing with the ultrasound-imaging system 100, which optical-fiber stylet 156, in turn, is configured to be inserted into a lumen of a medical device such as the needle 112 and convey the input optical signals from the optical interrogator 154 to a number of FBG sensors along a length of the optical-fiber stylet 156. The optical interrogator 154 is also configured to receive reflected optical signals conveyed by the optical-fiber stylet 156 reflected from the number of FBG sensors, the reflected optical signals indicative of a shape of the optical-fiber stylet 156. The optical interrogator 154 is also configured to convert the reflected optical signals into corresponding electrical signals for processing by the console 102 into distance and orientation information with respect to the target for dynamically adjusting a distance of the activated ultrasonic transducers 149, an orientation of the activated ultrasonic transducers 149, or both the distance and the orientation of the activated ultrasonic transducers 149 with respect to the target or the medical device when it is brought into proximity of the target. For example, the distance and orientation of the activated ultrasonic transducers 149 can be adjusted with respect to a blood vessel as the target. Indeed, an image plane can be established by the activated ultrasonic transducers 149 being perpendicular or parallel to the blood vessel in accordance with an orientation of the blood vessel. In another example, when a medical device such as the needle 112 is brought into proximity of the ultrasound probe 106, an image plane can be established by the activated ultrasonic transducers 149 being perpendicular to a medical-device plane including the medical device as shown in FIGS. 11-13 and 21-23 or parallel to the medical-device plane including the medical device for accessing the target with the medical device. The image plane can be perpendicular to the medical-device plane upon approach of the medical device and parallel to the medical-device plane upon insertion of the medical device (e.g., percutaneous puncture with the needle 112). The distance and orientation information can also be used for displaying an iconographic representation of the medical device on the display.

FIG. 2 shows that the ultrasound probe 106 further includes a button and memory controller 138 for governing button and ultrasound probe 106 operation. The button and memory controller 138 can include non-volatile memory (e.g., EEPROM). The button and memory controller 138 is in operable communication with a probe interface 140 of the console 102, which includes an input/output ("I/O") component 142 for interfacing with the ultrasonic transducers 148 and a button and memory I/O component 144 for interfacing with the button and memory controller 138.

The ultrasound probe 106 can include a magnetic-sensor array 146 for detecting a magnetized medical device such as the needle 112 during ultrasound-based medical procedures. The magnetic-sensor array 146 includes a number of magnetic sensors 150 embedded within or included on a housing of the ultrasound probe 106. The magnetic sensors 150 are configured to detect a magnetic field or a disturbance in a magnetic field as magnetic signals associated with the magnetized medical device when it is in proximity to the magnetic-sensor array 146. The magnetic sensors 150 are also configured to convert the magnetic signals from the magnetized medical device (e.g., the needle 112) into electrical signals for the console 102 to process into distance and orientation information for the magnetized medical device with respect to the predefined target, as well as for display of an iconographic representation of the magnetized medical device on the display screen 104 (see the magnetic field B of the needle 112 in FIG. 3). Thus, the magnetic-sensor array 146 enables the ultrasound-imaging system 100 to track the needle 112 or the like.

Though configured here as magnetic sensors, it is appreciated that the magnetic sensors 150 can be sensors of other types and configurations. Also, though they are described herein as included with the ultrasound probe 106, the magnetic sensors 150 of the magnetic-sensor array 146 can be included in a component separate from the ultrasound probe 106 such as a sleeve into which the ultrasound probe 106 is inserted or even a separate handheld device. The magnetic sensors 150 can be disposed in an annular configuration about the probe head 114 of the ultrasound probe 106, though it is appreciated that the magnetic sensors 150 can be arranged in other configurations, such as in an arched, planar, or semi-circular arrangement.

Each magnetic sensor of the magnetic sensors 150 includes three orthogonal sensor coils for enabling detection of a magnetic field in three spatial dimensions. Such 3-dimensional ("3-D") magnetic sensors can be purchased, for example, from Honeywell Sensing and Control of Morristown, NJ. Further, the magnetic sensors 150 are configured as Hall-effect sensors, though other types of magnetic sensors could be employed. Further, instead of 3-D sensors, a plurality of 1-dimensional ("1-D") magnetic sensors can be included and arranged as desired to achieve 1-, 2-, or 3-D detection capability.

Five magnetic sensors 150 are included in the magnetic-sensor array 146 so as to enable detection of a magnetized medical device such as the needle 112 in three spatial dimensions (e.g., X, Y, Z coordinate space), as well as the pitch and yaw orientation of the magnetized medical device itself. Detection of the magnetized medical device in accordance with the foregoing when the magnetized medical device is brought into proximity of the ultrasound probe 106 allows for dynamically adjusting a distance of the activated ultrasonic transducers 149, an orientation of the activated ultrasonic transducers 149, or both the distance and the orientation of the activated ultrasonic transducers 149 with respect to the target or the magnetized medical device. For example, the distance and orientation of the activated ultrasonic transducers 149 can be adjusted with respect to a blood vessel as the target. Indeed, an image plane can be established by the activated ultrasonic transducers 149 being perpendicular or parallel to the blood vessel in accordance with an orientation of the blood vessel. In other embodiments, fewer than five or more than five magnetic sensors of the magnetic sensors 150 can be employed in the magnetic-sensor array 146. More generally, it is appreciated that the number, size, type, and placement of the magnetic sensors 150 of the magnetic-sensor array 146 can vary from what is explicitly shown here.

As shown in FIG. 2, the ultrasound probe 106 can further include an inertial measurement unit ("IMU") 158 or any one or more components thereof for inertial measurement selected from an accelerometer 160, a gyroscope 162, and a magnetometer 164 configured to provide positional-tracking data of the ultrasound probe 106 to the console 102 for stabilization of an image plane. The processor 116 is further configured to execute the logic 120 for processing the positional-tracking data for adjusting the distance of the activated ultrasonic transducers 149 from the target, the orientation of the activated ultrasonic transducers 149 to the target, or both the distance and the orientation of the activated ultrasonic transducers 149 with respect to the target to maintain the distance and the orientation of the activated ultrasonic transducers 149 with respect to the target when the ultrasound probe 106 is inadvertently moved with respect to the target.

It is appreciated that a medical device of a magnetizable material enables the medical device (e.g., the needle 112) to be magnetized by a magnetizer, if not already magnetized, and tracked by the ultrasound-imaging system 100 when the magnetized medical device is brought into proximity of the magnetic sensors 150 of the magnetic-sensor array 146 or inserted into the body of the patient P during an ultrasound-based medical procedure. Such magnetic-based tracking of the magnetized medical device assists the clinician in placing a distal tip thereof in a desired location, such as in a lumen of a blood vessel, by superimposing a simulated needle image representing the real-time distance and orientation of the needle 112 over an ultrasound image of the body of the patient P being accessed by the magnetized medical device. Such a medical device can be stainless steel such as SS 304 stainless steel; however, other suitable needle materials that are capable of being magnetized can be employed. So configured, the needle 112 or the like can produce a magnetic field or create a magnetic disturbance in a magnetic field detectable as magnetic signals by the magnetic-sensor array 146 of the ultrasound probe 106 so as to enable the distance and orientation of the magnetized medical device to be tracked by the ultrasound-imaging system 100 for dynamically adjusting the distance of the activated ultrasonic transducers 149, an orientation of the activated ultrasonic transducers 149, or both the distance and the orientation of the activated ultrasonic transducers 149 with respect to the magnetized medical device.

During operation of the ultrasound-imaging system 100, the probe head 114 of the ultrasound probe 106 is placed against skin of the patient P. An ultrasound beam 152 is produced so as to ultrasonically image a portion of a target such as a blood vessel beneath a surface of the skin of the patient P. The ultrasonic image of the blood vessel can be depicted and stabilized on the display screen 104 of the ultrasound-imaging system 100.

Referring now to FIG. 3, an embodiment of an ultrasound probe that may be included in the ultrasound-imaging system of FIG. 1 is shown in accordance with some embodiments. The ultrasound probe 106 includes a probe head 114 that houses a mounted linear array of the ultrasonic transducers 148 or a 2-D array of the ultrasonic transducers 148, wherein the ultrasonic transducers 148 are piezoelectric transducers or capacitive micromachined ultrasonic transducers ("CMUTs"). When the ultrasound probe 106 is configured with the 2-D array of the ultrasonic transducers 148, a subset of the ultrasonic transducers 148 is linearly activated as needed for ultrasound imaging in accordance with ultrasound-imaging data, magnetic-field data, shape-sensing data, or a combination thereof to maintain the target in an image plane or switch to a different image plane (e.g., from perpendicular to a medical-device plane to parallel to the medical-device plane) including the target.

The probe head 114 is configured for placement against skin of the patient P proximate a prospective needle-insertion site where the activated ultrasonic transducers 149 in the probe head 114 can generate and emit the generated ultrasound signals into the patient P in a number of pulses, receive reflected ultrasound signals or ultrasound echoes from the patient P by way of reflection of the generated ultrasonic pulses by the body of the patient P, and convert the reflected ultrasound signals into corresponding electrical signals for processing into ultrasound images by the console 102 to which the ultrasound probe 106 is communicatively coupled. In this way, a clinician can employ the ultrasound-imaging system 100 to determine a suitable insertion site and establish vascular access with the needle 112 or another medical device.

The ultrasound probe 106 may further include the control buttons 110 for controlling certain aspects of the ultrasound-imaging system 100 during an ultrasound-based medical procedure, thus eliminating the need for the clinician to reach out of a sterile field around the patient P to control the ultrasound-imaging system 100. For example, a control button of the control buttons 110 can be configured to select or lock onto the target (e.g., a blood vessel, an organ, etc.) when pressed for visualization of the target in preparation for inserting the needle 112 or another medical device into the target. Such a control button can also be configured to deselect the target, which is useful whether the target was selected by the control button, or another means such as by holding the ultrasound probe 106 stationary over the target to select the target, issuing a voice command to select the target, or the like.

Further, the ultrasound probe 106 as illustrated in FIG. 3 includes an inertial measurement unit ("IMU") 158. As discussed above, the IMU 158 is configured to obtain inertial measurement from any of one or more components selected from an accelerometer 160, a gyroscope 162, and a magnetometer 164. Based on the obtained inertial measurements, the IMU 158 is configured to provide positional-tracking data of the ultrasound probe 106 to the console 102 thereby enabling spatial awareness of the probe 106. For instance, the positional-tracking data may be recorded from a starting time (i.e., when the probe 106 is positioned at or adjacent to an insertion site) until an end time (i.e., when the probe 106 is positioned above a target placement position, where the probe 106 sits external to the patient P with the target placement position being internal to the patient P, such as with the vasculature). Alternatively, the positional-tracking data may be recorded at time intervals such as every 2, 5, 10, etc., seconds from the starting time until the end time. In such embodiments, a user may indicate the starting and end times through any type of user input. The positional-tracking data may also be utilized to provide alternative reality (any of augmented reality, virtual reality, and/or mixed reality) displays to a user (e.g., a medical professional) to assist in determining an insertion pathway.

The processor 116 may be configured to execute the logic 120 for processing the positional-tracking data to determine a length of an insertion pathway from the insertion site to the target placement position. For instance, the processor may utilize the positional-tracking data to determine a distance traveled by the probe 106 as a user moves the probe 106 from the insertion site to the position above the target placement position. As will be discussed in further detail below, the length of the insertion pathway may assist in determining or computing: an anticipated length of a medical device needed to enter the patient P at the insertion site and traverse the patient vasculature for disposition at the target placement position; a recommended trim length of the medical device; recommended device configurations; etc.

In addition to the positional-tracking data of the probe 106, additional data utilized in determining the anticipated length of the medical device, the recommended trim length, and recommended device configurations may include ultrasound data received from the probe 106 to determine a depth and size (e.g., circumstance) of the desired blood vessels and/or organs. The depth and size may be determined automatically by the logic 120 and/or via user input.

Figure 4:
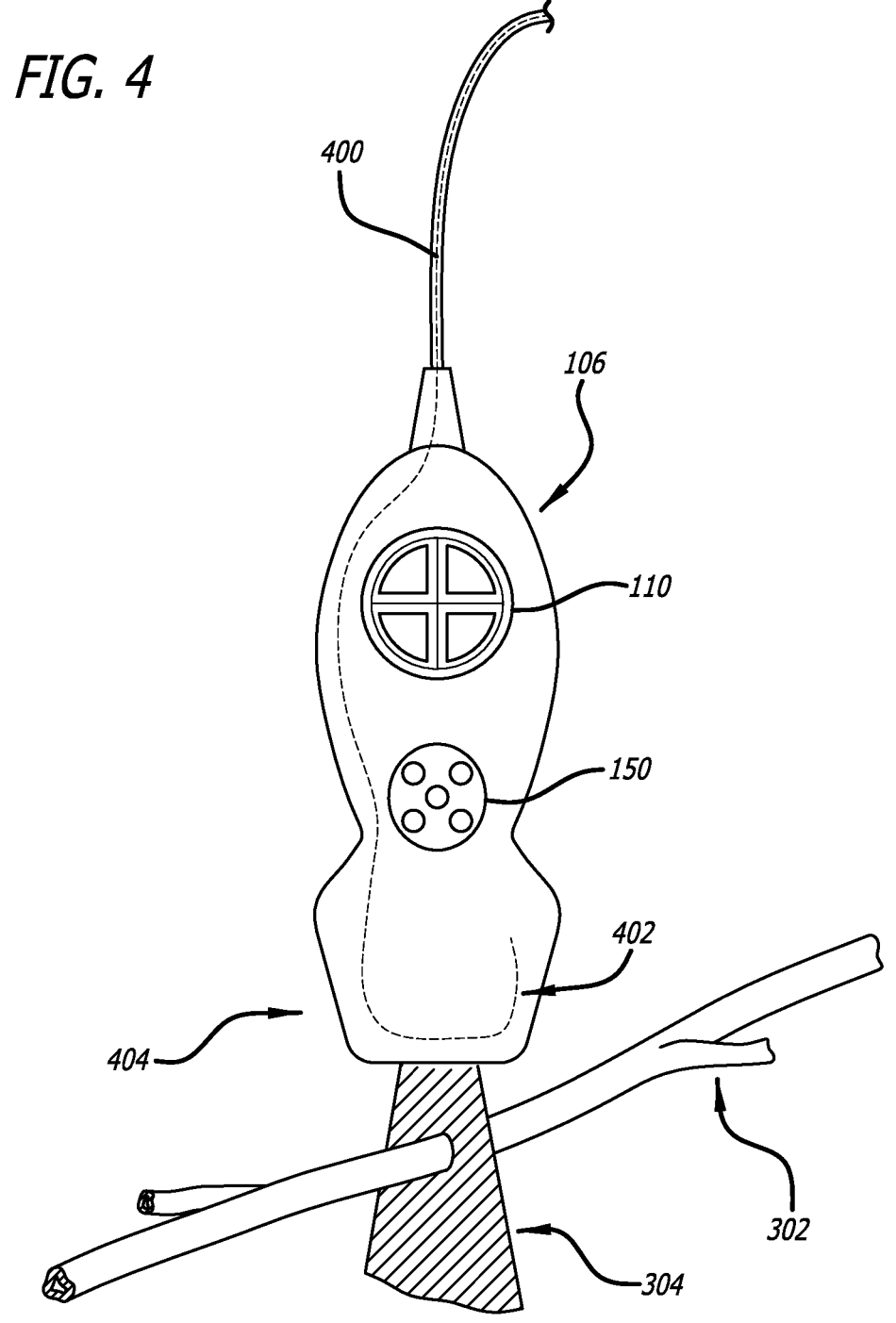
FIG. 4 illustrates an alternative embodiment to the ultrasound probe of FIG. 3 modified to include a multi-core optical fiber in accordance with some embodiments.

Referring now to FIG. 4, the ultrasound probe 106 is shown as being modified to include a multi-core optical fiber in accordance with some embodiments. The ultrasound probe 106 of FIG. 4 includes a multi-core optical fiber 400 that extends the length of a tether from the console 102 to the probe 106. Further, the multi-core optical fiber 400 may be configured in a predetermined geometry 402 at the distal end 404 of the probe 106. The predetermined geometry enables logic of the console 102 to perform shape sensing operations enabling detection of an orientation of the probe 106. More specifically, as the orientation of the predetermined geometry 402 relative to the transducers 148 is known prior to deployment of the probe 106, the ultrasound image displayed on the display 104 may be augmented with certain information, e.g., mirror coordination correction information, color-coding information, highlighting of a target vessel, and the probe 106 may provide directional instructions via haptic feedback. Without knowing the orientation of the probe 106, such information cannot be provided.

Figure 5:
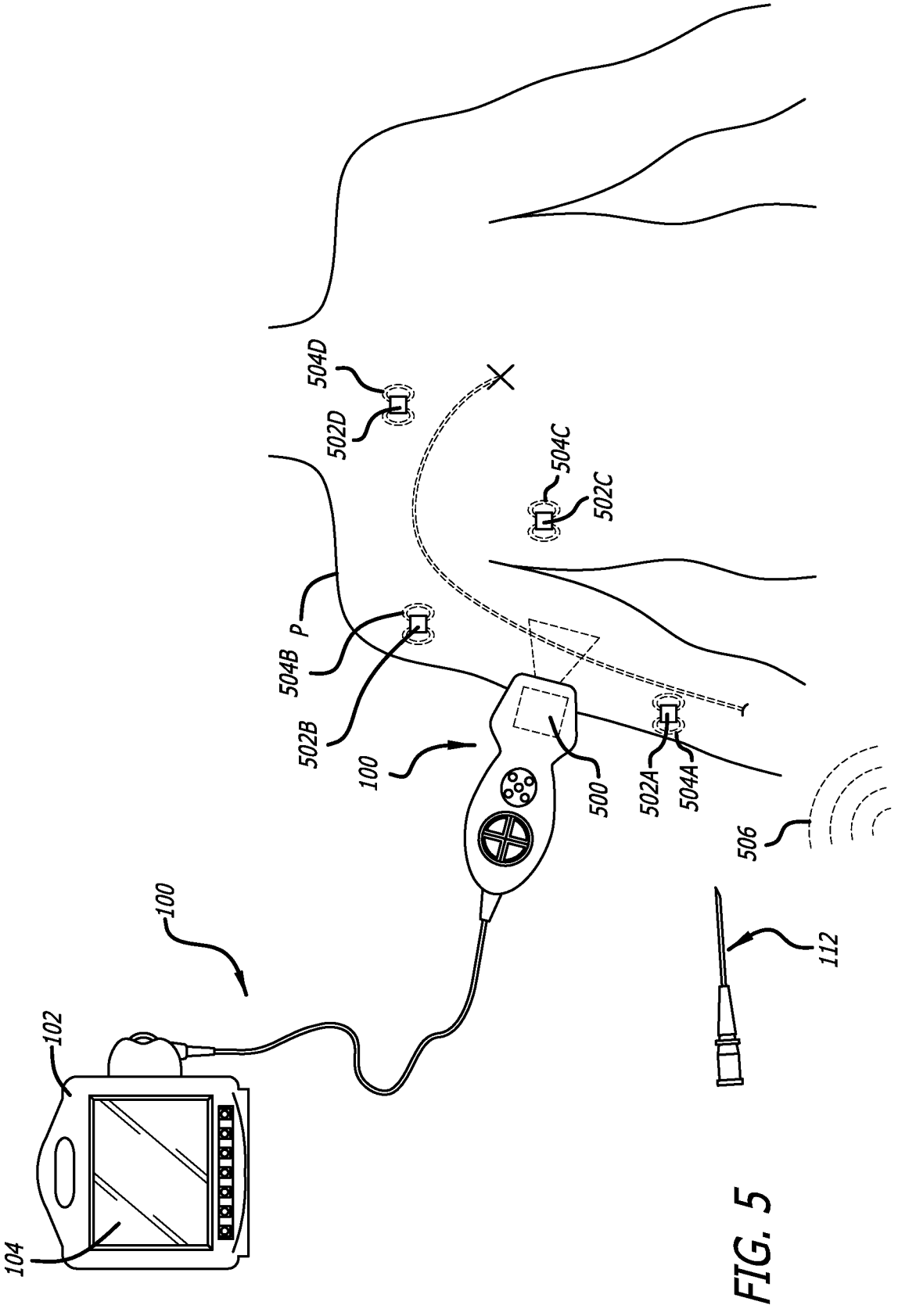
FIG. 5 illustrates an alternative embodiment to the ultrasound probes of FIGS. 3-4 modified to include a magnetic sensor in accordance with some embodiments.

Referring to FIG. 5, an illustration of an alternative embodiment to the ultrasound probes of FIGS. 3-4 modified to include a magnetic sensor is shown in accordance with some embodiments. The system 100 as illustrated in FIG. 5 includes the probe 106 modified to include a magnetic sensor 500 configured to detect magnetic fields 504A-504D generated by the magnetic targets 502A-502D and/or an ambient magnetic field 506 such as the Earth's magnetic field. As the probe 106 is moved along a path from a starting position adjacent the insertion site S to a position above the target placement position (e.g., see positions 900, 904 and the path traveled 906 of FIG. 9), the magnetic sensor 500 detects the magnetic fields 504A-504D and/or the magnetic field 506 thereby enabling the logic 120 to determine positional-tracking data corresponding to the movement of the probe 106. More specifically, as the targets 502A-502D have known positions on the patient body, the positional-tracking data may be assembled by the variations in the strength of the detected magnetic fields 504A-504D. Alternatively, or in addition, the variations in the strength of the magnetic field 506 may be recorded as the probe 106 is moved.

Figure 6:
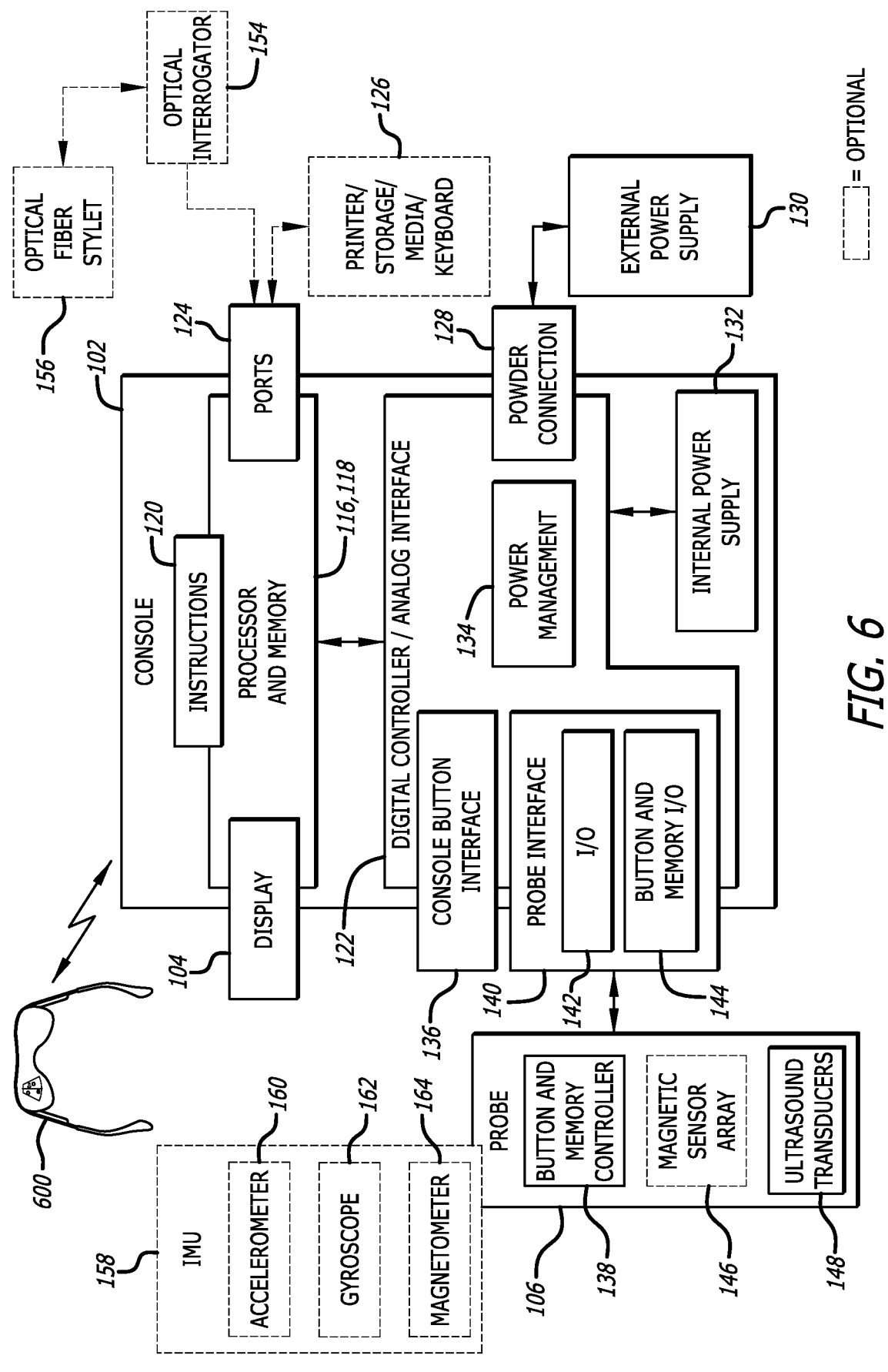
FIG. 6 provides a block diagram for an ultrasound probe connected to a console of the anatomy-visualizing system in accordance with some embodiments.

Referring to FIG. 6, a block diagram of an ultrasound system including a console connected to an ultrasound probe and an alternative reality device is shown in accordance with some embodiments. Many of the components illustrated in FIG. 6 are present in FIG. 2 and discussed above. As a result, those components and their respective functionalities and configurations will not be discussed again, unless the embodiment of FIG. 6 includes additional functionality and/or configurations.

In particular, the system of FIG. 6 illustrates that the ultrasound system discussed above may include an alternative reality (AR) device connected thereto. In some instances, the display 104 of the console 102 may provide AR data and the AR device 600 may provide secondary AR data as an alternative to the AR data provided by the display 104. The AR device 600 may be connected to the console 102 via a wired or wireless (shown) configuration. In some instances, the AR device 600 may connect to a cloud server and to the console 102 indirectly via the cloud server. In such an embodiment, the cloud server may process a portion of the logic 120 and/or the logic 120 processing on the console 102 may provide instructions to the AR device 600 via the cloud server.

Figure 7:
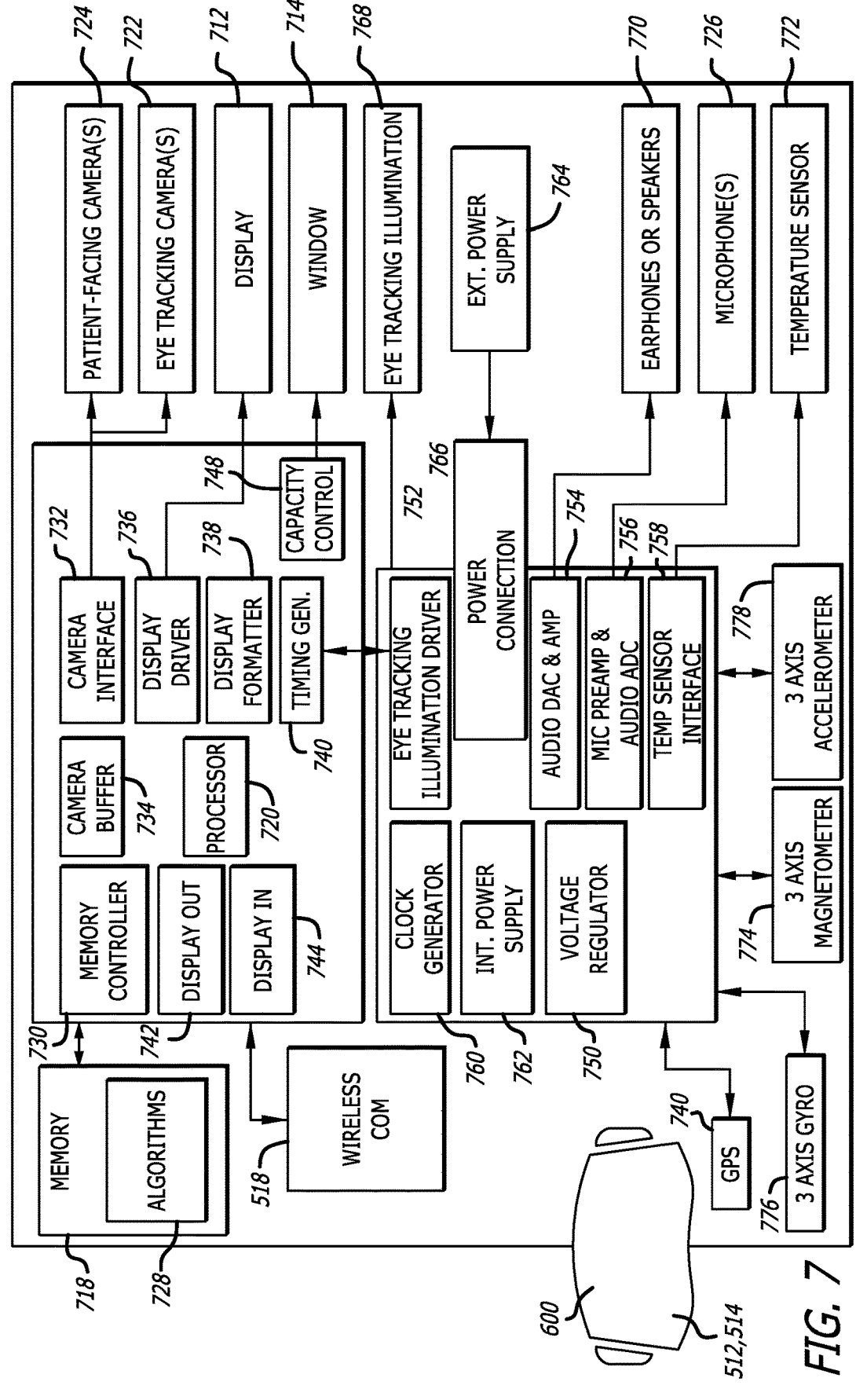
FIG. 7 provides a block diagram for an alternative-reality headset of the anatomy-visualizing system in accordance with some embodiments.

Referring to FIG. 7, a block diagram for an alternative-reality headset of the anatomy-visualizing system is shown in accordance with some embodiments. FIG. 7 illustrates that the AR device 600 may have an alternative form-factor than the glasses of FIGS. 6, 8. In particular, the AR device 600 may take a goggle-type or face shield-type form factor, includes a suitably configured display screen 712 and a window 714 thereover coupled to a frame 716 having electronic circuitry including memory 718 and one or more processors 720. The display screen 712 is configured such that a wearer of the AR device 600 can see an environment (e.g., operating room) including the patient through the display screen 712 in accordance with an opacity of the window 714, which opacity is adjustable with an opacity control 748. The display screen 712 is configured to display objects of virtual anatomy over the environment such as over the patient, the objects of virtual anatomy corresponding to the ultrasound-image segments produced by the console 110 with the image segmentation algorithm. In displaying the objects of virtual anatomy over the environment, the AR device 600 can be configured to three-dimensionally anchor the objects of virtual anatomy to the environment such as to the patient over which the objects of virtual anatomy are displayed, which allows the wearer of the AR device 600 to see a true representation of the patient's anatomy for one or more subsequent medical procedures (e.g., accessing a vessel and placing a medical device such as a guidewire of catheter in the vessel). Anchoring the objects of virtual anatomy to the environment or to the patient over which the objects of virtual anatomy are displayed is characteristic of mixed reality.

The AR device 600 can further include a perceptual user interface ("PUT") configured to enable the wearer of the AR device 600 to interact with the AR device 600 without a physical input device such as keyboard or mouse. Instead of a physical input device, the PUI can have input devices including, but not limited to, one or more wearer-facing eye-tracking cameras 722, one or more patient-facing cameras 724, one or more microphones 726, or a combination thereof. At least one advantage of the PUI the input devices thereof is the clinician does not have to reach outside a sterile field to execute a command of the AR device 600.

With respect to the one or more eye-tracking cameras 722, the one or more eye-tracking cameras 722 can be coupled to the frame 716 and configured to capture eye movements of the wearer in a camera buffer 734 or the memory 718. The processor 720 of the AR device 600 can be configured to process the eye movements with an eye-movement algorithm of one or more algorithms 728 to identify a focus of the wearer for selecting the objects of virtual anatomy or other representations (e.g., outlines of medical device, virtual medical devices, etc.) corresponding to the focus of the wearer. For example, the focus of the wearer can be used by the PUI to select an object of virtual anatomy for enhancing the object of virtual anatomy by way of highlighting the object of virtual anatomy or increasing the contrast between the object of virtual anatomy and its environment. In another example, the focus of the wearer can be used by the PUI to select an object of virtual anatomy for performing one or more other operations of the PUI such as zooming in on the object of virtual anatomy, providing a cross-section of the one or more objects of virtual anatomy, or the like.

With respect to the one or more patient-facing cameras 724, the one or more patient-facing cameras 724 can be coupled to the frame 716 and configured to capture gestures of the wearer in a camera buffer 734 or the memory 718. The processor 720 of the AR device 600 can be configured to process the gestures with a gesture-command algorithm of the one or more algorithms 728 to identify gesture-based commands issued by the wearer for execution thereof by the AR device 600.

With respect to the one or more microphones 726, the one or more microphones 726 can be coupled to the frame 716 configured to capture audio of the wearer in the memory 718. The processor 720 of the AR device 600 can be configured to process the audio with an audio-command algorithm of the one or more algorithms 728 to identify audio-based commands issued by the wearer for execution thereof by the AR device 600.

The electronic circuitry includes the processor 720, a memory controller 730 in communication with the memory 718 (e.g., dynamic random-access memory ["DRAM"]), a camera interface 732, the camera buffer 734, a display driver 736, a display formatter 738, a timing generator 740, a display-out interface 742, and a display-in interface 744. Such components can be in communication with each other through the processor 720, dedicated lines of one or more buses, or a combination thereof.

The camera interface 216 is configured to provide an interface to the one or more eye-tracking cameras 722 and the one or more patient-facing cameras 724, as well as store respective images received from the cameras 722, 724 in the camera buffer 734 or the memory 718. Each camera of the one or more eye-tracking cameras 722 can be an infrared ("IR") camera or a position-sensitive detector ("PSD") configured to track eye-glint positions by way of IR reflections or eye glint-position data, respectively.

The display driver 220 is configured to drive the display screen 712. The display formatter 738 is configured to provide display-formatting information for the objects of virtual anatomy to the one or more processors 414 of the console 110 for formatting the objects of virtual anatomy for display on the display screen 712 over the environment such as over the patient. The timing generator 740 is configured to provide timing data for the AR device 600. The display-out interface 742 includes a buffer for providing images from the one or more eye-tracking cameras 722 or the one or more patient-facing cameras 724 to the one or more processors 414 of the console 110. The display-in interface 744 includes a buffer for receiving images such as the objects of virtual anatomy to be displayed on the display screen 712. The display-out and display-in interfaces 742, 744 are configured to communicate with the console 110 by way of wireless communications interface 746. The opacity control 748 is configured to change a degree of opacity of the window 714.

Additional electronic circuitry includes a voltage regulator 750, an eye-tracking illumination driver 752, an audio digital-to-analog converter ("DAC") and amplifier 754, a microphone preamplifier and audio analog-to-digital converter ("ADC") 756, a temperature-sensor interface 758, and a clock generator 760. The voltage regulator 750 is configured to receive power from an internal power supply 762 (e.g., a battery) or an external power supply 764 through power connection 766. The voltage regulator 750 is configured to provide the received power to the electronic circuitry of the AR device 600. The eye-tracking illumination driver 236 is configured to control an eye-tracking illumination unit 768 by way of a drive current or voltage to operate about a predetermined wavelength or within a predetermined wavelength range. The audio DAC and amplifier 754 is configured to provide audio data to earphones or speakers 770. The microphone preamplifier and audio ADC 756 is configured to provide an interface for the one or more microphones 726. The temperature sensor interface 758 is configured as an interface for a temperature sensor 772. In addition, the AR device 600 can include orientation sensors including a three-axis magnetometer 774, a three-axis gyroscope 776, and a three-axis accelerometer 778 configured to provide orientation-sensor data for determining an orientation of the AR device 600 at any given time. Furthermore, the AR device 600 can include a global-positioning system ("GPS") receiver 780 configured to receive GPS data (e.g., time and position information for one or more GPS satellites) for determining a location of the AR device 600 at any given time.

Figure 8:
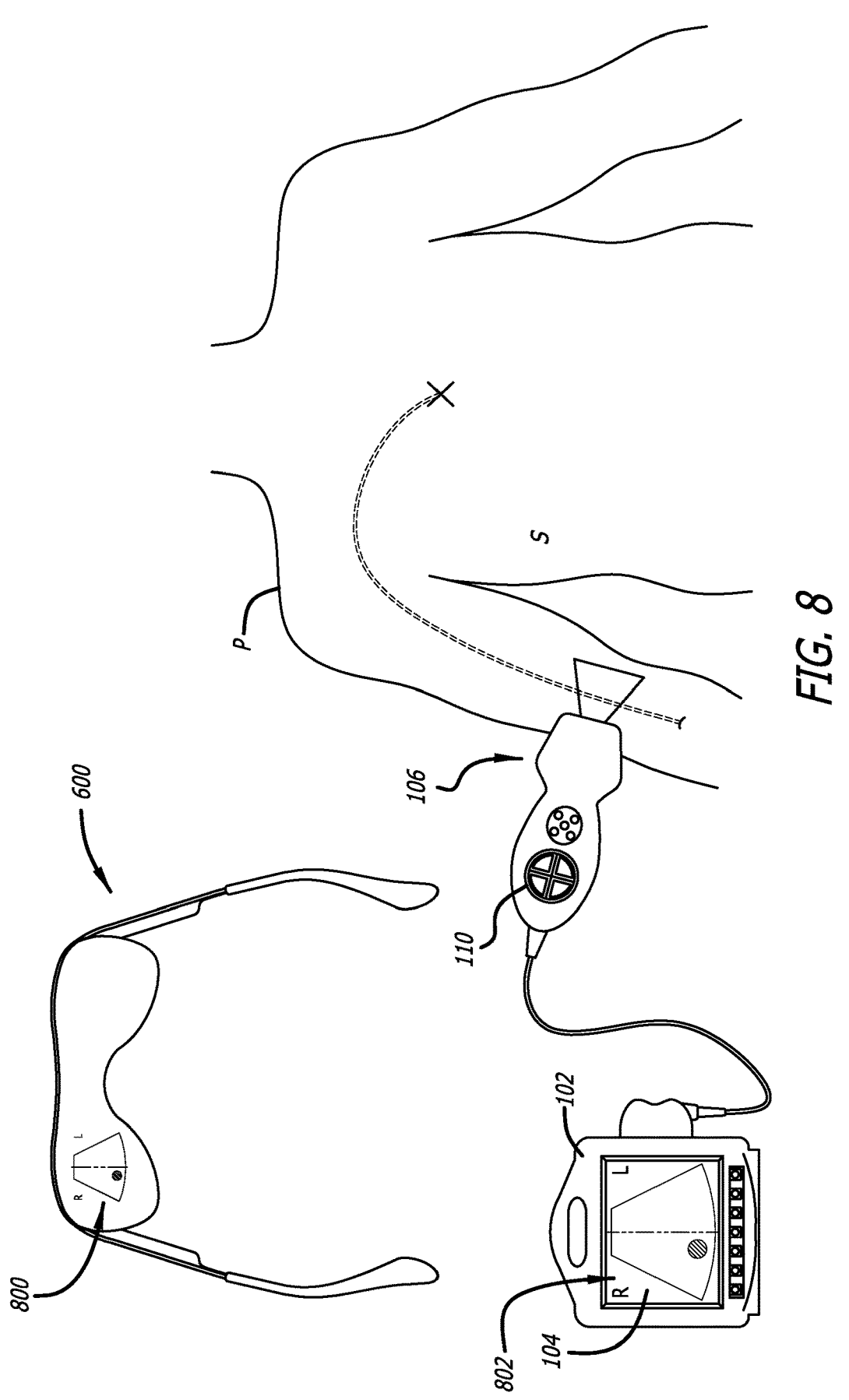
FIG. 8 illustrates objects of virtual anatomy over a patient as seen through a display screen of the alternative-reality headset in accordance with some embodiments.

Referring to FIG. 8, objects of virtual anatomy over a patient as seen through a display screen of the alternative-reality headset are shown in accordance with some embodiments. The AR device 600 provides a second option (e.g., modality) for viewing AR data, while the first AR data 802 and secondary AR data 800 may the same or substantially the same. In one embodiment, the AR device 600 is represented by a pair of AR glasses to be worn by a clinician performing a procedure to determine the insertion pathway as well as the ultrasound procedure itself. The AR glasses 600 may be configured to display secondary AR data 800 on a display screen of the AR glasses 600. In the illustration of FIG. 8, the first and secondary AR data (802, 800) is substantially the same (e.g., substantially the same display). However, the secondary AR data 800 may be seen by the clinician as an overlay directly on the patient body. For example, when imaging the insertion site S, the clinician may view the insertion site S through the AR glasses 600 such that the ultrasound image including any of highlighting of detected anatomical features and/or directional or orientation markers also appear in an augmented manner. Thus, the clinician views the augmented ultrasound image directly on the patient body when viewing the patient body through the AR glasses 600. Advantageously, the AR glasses 600 enable the clinician to maintain eye contact on the imaging area of the patient body and the augmented ultrasound image may correct any mirrored coordination that would otherwise be present when viewing the ultrasound image on the display 104.

Further, as the clinician performs a procedure to determine the insertion pathway, the AR data may be displayed in real-time (or substantially real-time) which the vessels of the patient vasculature displayed as an overlay to the patient P by the AR glasses 600 (as AR data 800) and/or the display 104 (as AR data 802). Thus, as the clinician moves the probe 106 along the exterior of the patient P tracking the desired insertion pathway, the clinician may visualize the vasculature, thereby allowing the clinician to more accurately move the probe 106 along the exterior of the patient P while tracking the desired insertion pathway. For instance, based on the AR data, the clinician may more accurately track desired vessels comprising the desired insertion pathway.

In some embodiments, the AR data may augment the virtual vasculature with the display of a virtual medical device (e.g., a catheter, guidewire, or stylet) thereby enabling the clinician to virtually visualize the medical device traversing the patient vasculature along the desired insertion pathway.

As noted above, the procedure to determine the insertion pathway may include a clinician moving the ultrasound probe along an external portion of the patient P while the probe 106 images the vasculature thereby "tracing" the desired insertion pathway to be taken by an inserted medical device. The ultrasound data obtained by the probe 106 and the positional-tracking data obtained via the IMU 158, multi-core optical fiber 400, and/or the magnetic sensor 500 as discussed above, which may be combined and transformed into AR data for display either on the display 104 and/or the AR glasses 600.

Figure 9:
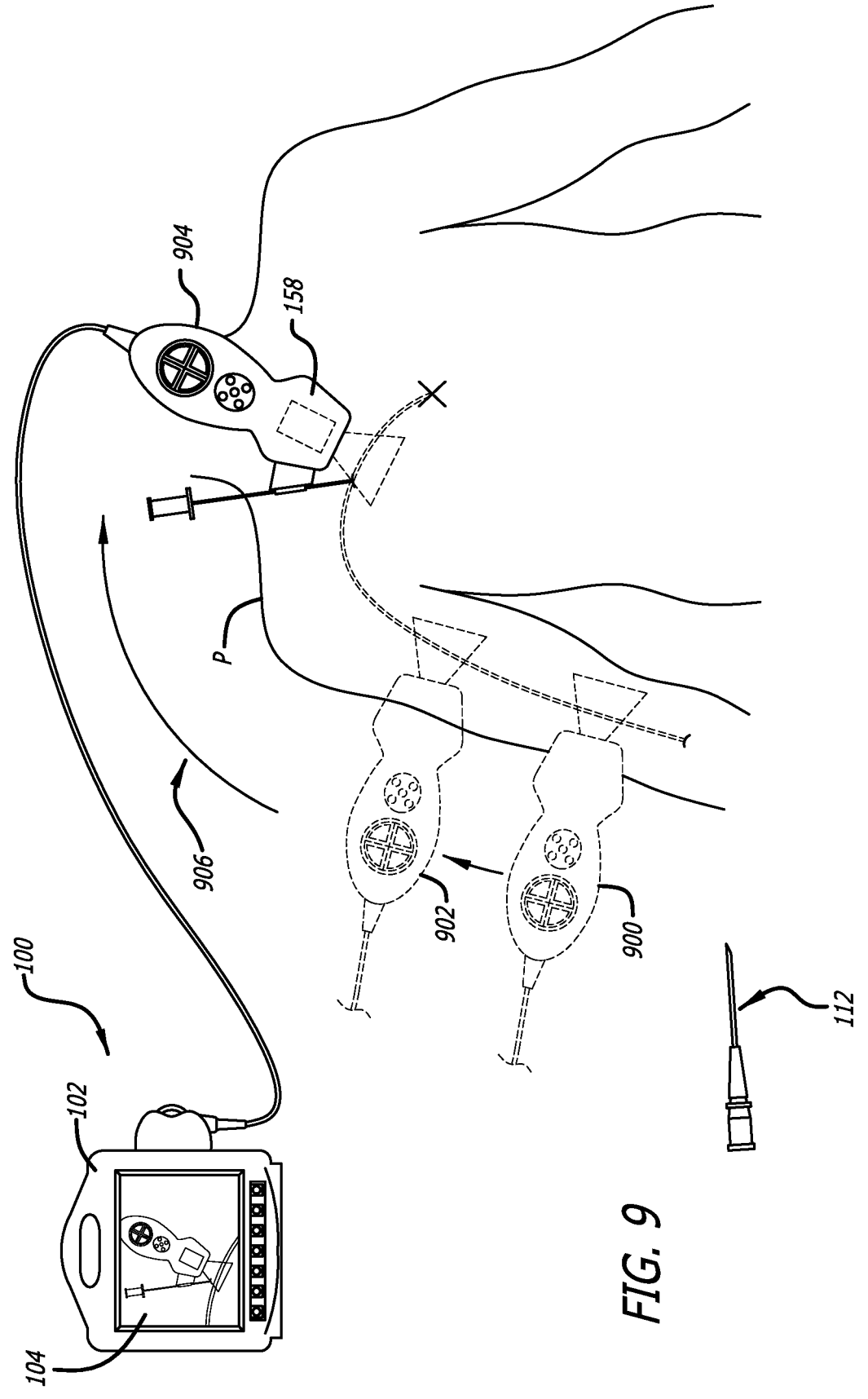
FIG. 9 illustrates a sample implementation of an ultrasound system including an ultrasound probe configured with an inertial measurement unit ("IMU") as shown in FIG. 3 in accordance with some embodiments.

Referring to FIG. 9, a sample implementation of an ultrasound system including an ultrasound probe configured with a IMU as illustrated in FIG. 3 is shown in accordance with some embodiments. The illustration of the implementation of the ultrasound system 100 provides multiple discussion points. First, multiple positions of the probe 106 are shown, positions 900, 902, 904, where FIG. 9 is intended to illustrate the movement of the probe 106 while tracking the insertion pathway from a starting position, position 900, that is adjacent to the insertion site S, to a second position, position 902, to a third position, position 904, that is above the target placement position of a medical device (e.g., the superior vena cava (SVC)). Of course, it should be understood that the three positions are merely exemplary and that any points along the path traveled 906 by the probe 106 in tracking the insertion pathway may be considered a position. The positional-tracking data may be recorded for the probe 106 during the entirety of the tracking as the probe 106 moves from position 900 to position 904. However, the positional-tracking data may be recorded at certain intervals such as time intervals or distance intervals. FIG. 9 illustrates the use of the IMU 158 to obtain the positional-tracking data; however, the embodiments of the probe 106 as discussed in FIGS. 4-5 may also be utilized in determining positional-tracking data.

Second, the illustration of the implementation in FIG. 9 details one sample graphical user interface (GUI) 908 that may be generated and displayed by the logic 120 on the display 104 of the console 102. For example, the GUI 908 may include a three-dimensional (3D) rendering of the patient body illustrating the imaged vasculature along the path traveled 906. The GUI 908 may include a graphic of the needle 112 that is to be inserted at the insertion site S. In some embodiments, the GUI 908 may be configured to receive user input in any of the manners described herein corresponding to selection of an imaged vessel, where the selection of imaged vessels comprises the insertion pathway. Thus, the clinician is capable of visually building an insertion pathway while imaging the patient P. The insertion pathway built by the clinician may be used in place of the positional-tracking data to determine the anticipated length of a medical device needed to enter the patient P at the insertion site and traverse the patient vasculature for disposition at the target placement position, the recommended trim length of the medical device; recommended device configurations, etc. In other embodiments, the insertion pathway built by the clinician may be to confirm the anticipated length of a medical device needed to enter the patient P at the insertion site and traverse the patient vasculature for disposition at the target placement position, the recommended trim length of the medical device; recommended device configurations, etc. as determined by the logic 120 from the positional-tracking data.

Third, the GUI 908 may also include a listing 910 of the results of the analyses performed by the logic 120 in the form of the anticipated length of a medical device needed to enter the patient P at the insertion site and traverse the patient vasculature for disposition at the target placement position, the recommended trim length of the medical device; recommended device configurations, etc.

Figure 10:
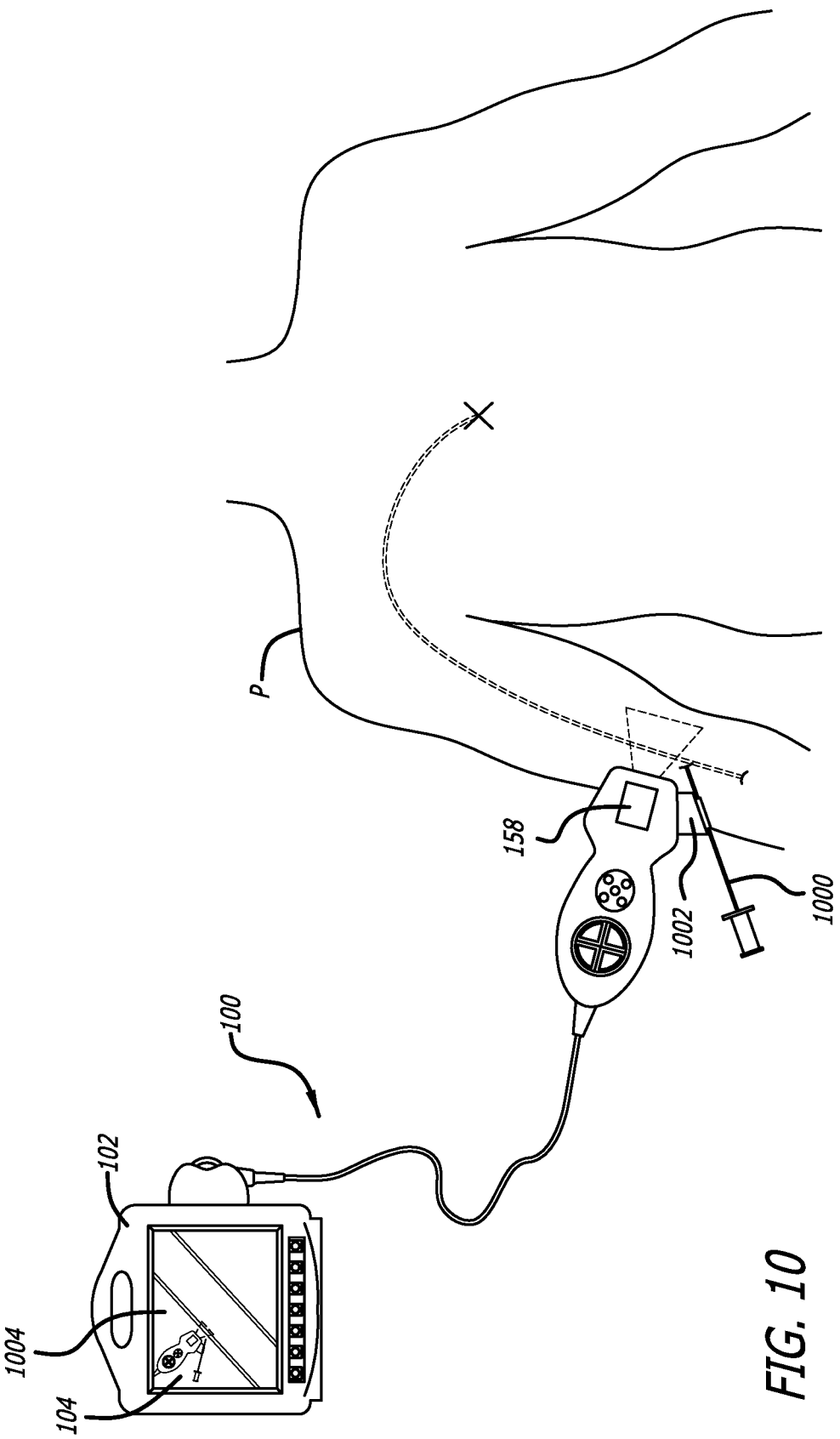
FIG. 10 illustrates results of an analysis performed during or after the implementation shown in FIG. 9 including providing a digital frame of reference for insertion of a medical device in accordance with some embodiments.

Referring to FIG. 10, results of an analysis performed during or after the implementation shown in FIG. 9 including providing a digital frame of reference for insertion of a medical device are shown in accordance with some embodiments. Given the positional-tracking data, the logic 120 may utilize the starting position of the probe 106 (e.g., position 900 of FIG. 9) as reference data for supplying additional information to the clinician such as a projected needle insertion path based on the starting position and the orientation (e.g., angling) of the probe 106. For instance, the display 104 may display a graphic 1004 illustrating a projected needle insertion path based on the tracking of the insertion pathway (e.g., movement along the path traveled 906 as shown in FIG. 9). When the probe 106 is returned to the starting position, real-time positional-tracking data may be used to display an updated projected needle insertion path. In some embodiments, the updated projected needle insertion path and the orientation of the probe 106 may be overlaid on the previously projected needle insertion path and the orientation of the probe 106 so that the clinician may align and orient the probe according to the positional-tracking data (or make updates as necessary).

Figure 11A:
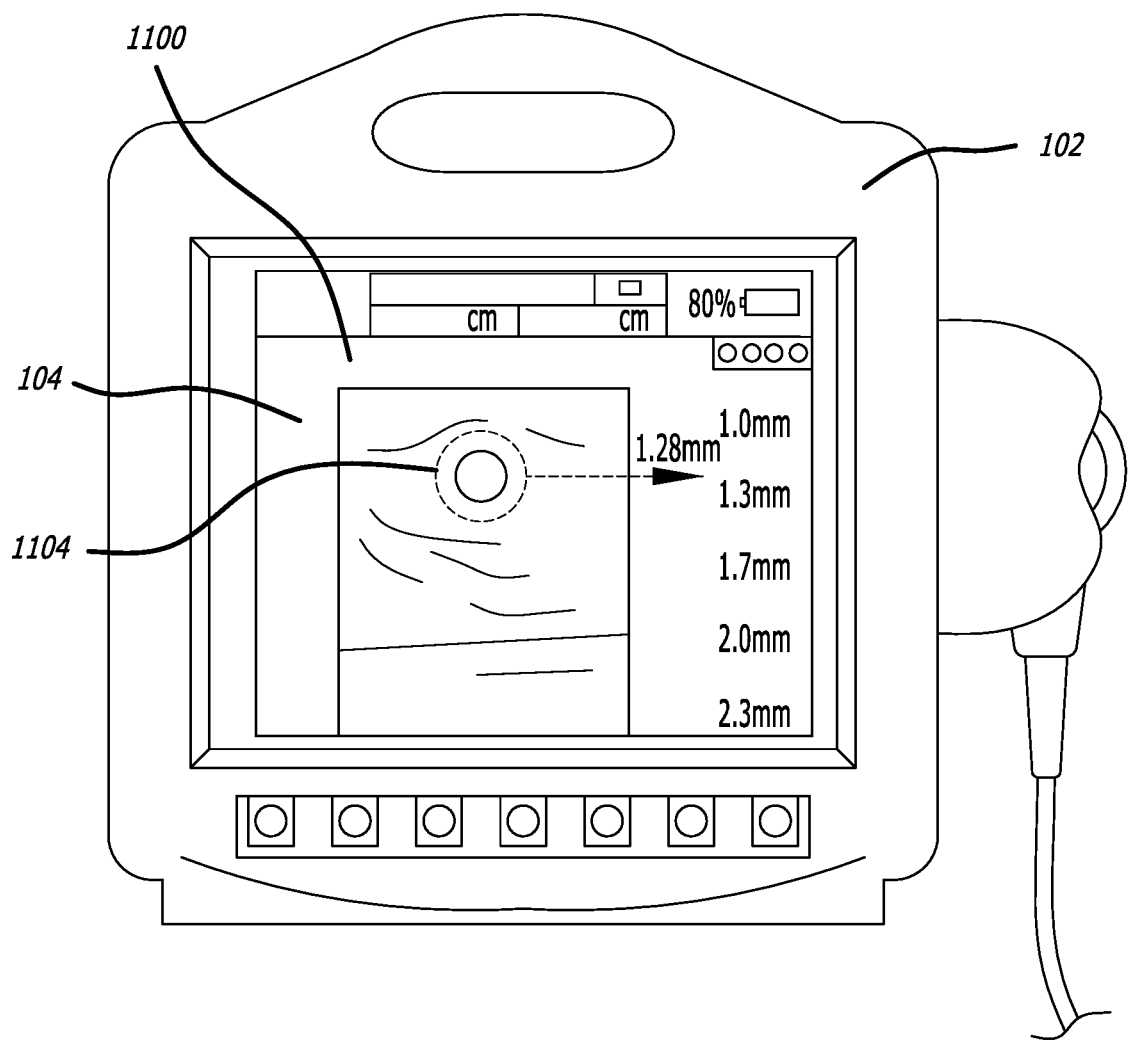
FIGS. 11A-11B illustrate the refinement of analyses performed and/or results obtained by an ultrasound system during or after implementation as shown in FIGS. 9-10 in accordance with some embodiments.
Figure 11B:
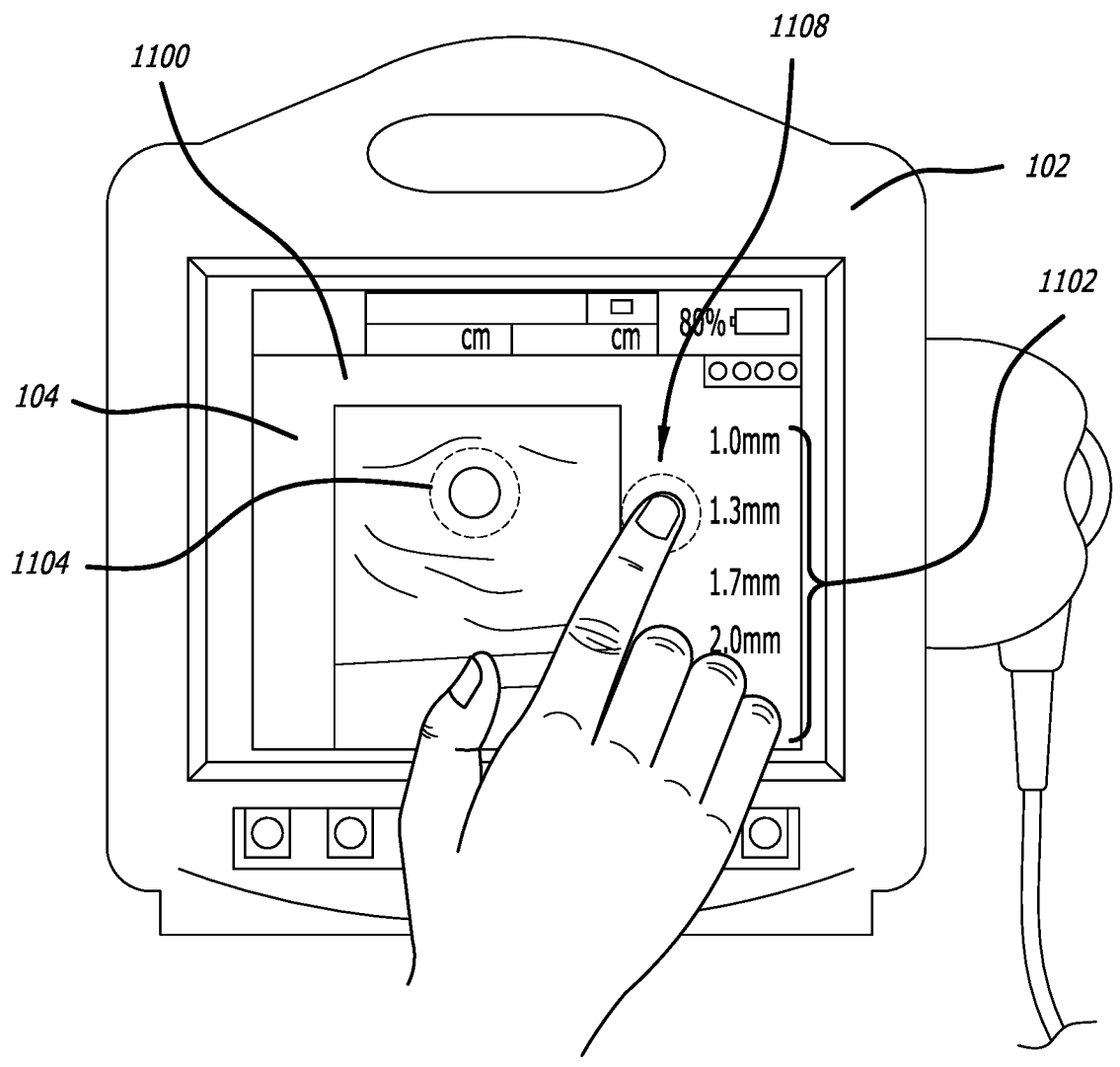

Referring to FIGS. 11A-11B, a first refinement of analyses performed and/or results obtained by the ultrasound system during or after implementation as shown in FIGS. 9-10 are shown in accordance with some embodiments. FIG. 11A illustrates a first graphical user interface rendered on the display 104 of the console 102. As noted above, in additional to the use of positional-tracking data of the probe 106, the logic 120 may utilize ultrasound data and/or user input to obtain certain information about the vasculature. As illustrated in FIG. 11A, the logic 120 has automatically detected a vessel 1104 being imaged and has determined a depth of the vessel under the patient skin. As an illustrative example, the graphical user interface may include an indicator (dotted lined) around detected vessel 1104 and an indicator 106 (dotted line) pointing toward a depth (e.g., 1.28 mm) within a depth scale 1102. The determined depth (128 mm) may be provided adjacent to the indicator 106; however, such need not appear or may appear in a different location. FIG. 11A provides merely one example of a graphical user interface that provides an illustration of refinement data utilized in determining an anticipated length of a medical device needed to enter the patient P at the insertion site and traverse the patient vasculature for disposition at the target placement position, a recommended trim length of the medical device, recommended device configurations, etc.

FIG. 11B illustrates a second graphical user interface rendered on the display 104 of the console 102. While FIG. 11A illustrates how refinement data is determined automatically, FIG. 11B illustrates how user input may contribute to the determination of refinement data. In particular, an ultrasound image similar to that displayed in FIG. 11A may be rendered on the display 104 of the console 102. In some instances, the logic 120 may automatically detect a vessel and provider an indicator 1104 as discussed above. However, in other embodiments, a user may provide user input, such as touching the display 104 (which may be a capacitive touch screen, an infrared touch screen, a resistive touch screen, or a surface acoustic wave touch screen), uses a stylus, via control buttons 150 of the probe 106, etc., to select, click on, outline, etc., the vessel, which results in the logic 120 forming the indicator 1104 around the vessel. Similarly, the user may provide user input via any of the methodologies discussed above to select a depth via the depth scale 1102.

Figure 12:
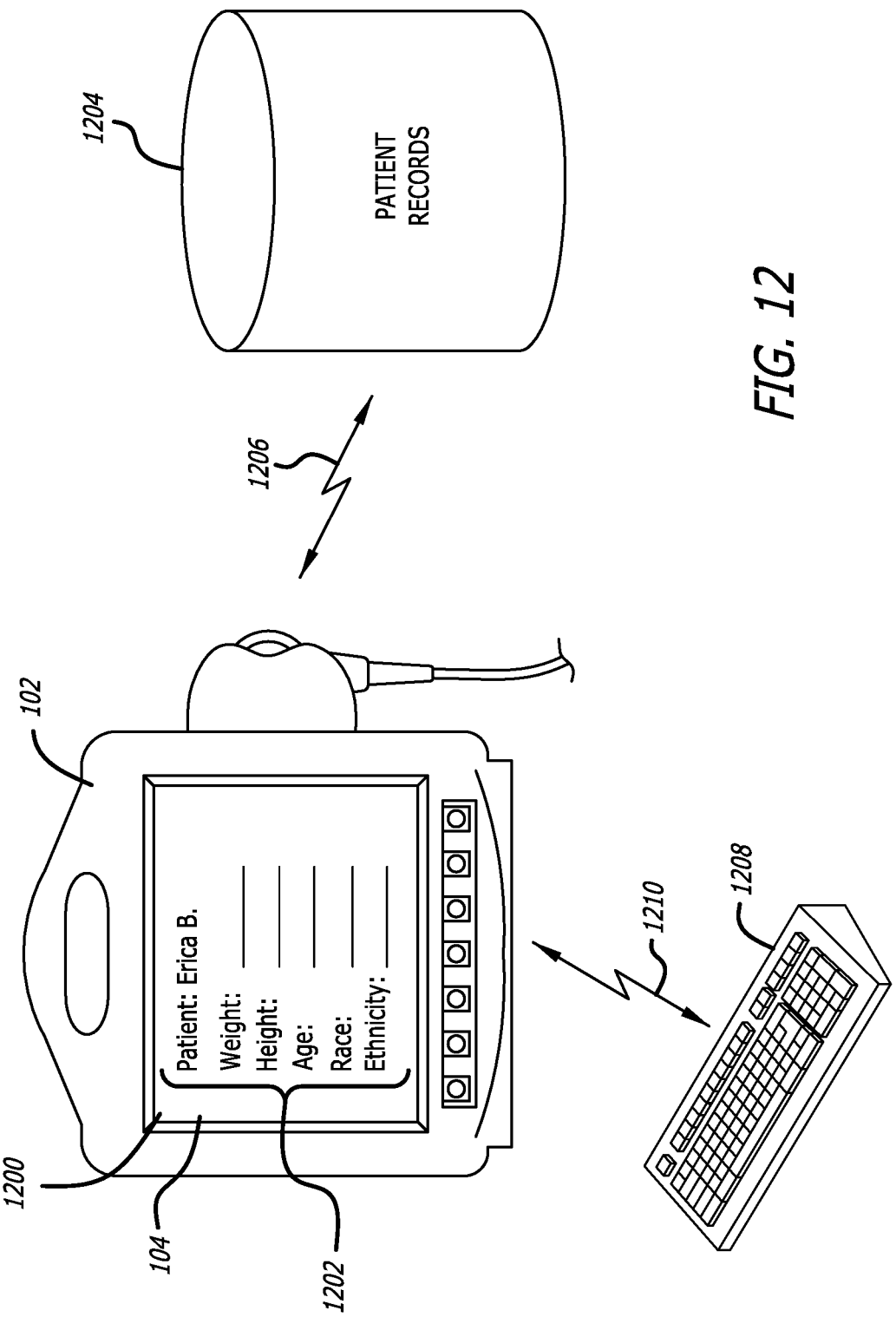
FIG. 12 illustrates a second refinement of analyses performed and/or results obtained by the ultrasound system during or after implementation as shown in FIGS. 9-10 based on anatomical and/or demographic considerations in accordance with some embodiments.

Referring to FIG. 12, a second refinement of analyses performed and/or results obtained by the ultrasound system during or after implementation as shown in FIGS. 9-10 based on anatomical and/or demographic considerations is shown in accordance with some embodiments. The second refinement of analyses performed and/or results obtained by the ultrasound system refers to the utilization of patient specific data to tailor the anticipated length of a medical device needed to enter the patient P at the insertion site and traverse the patient vasculature for disposition at the target placement position, the recommended trim length of the medical device, the recommended device configurations, etc., as discussed above.

In particular, patient specific data may factor into the analyses performed by the logic 120 in determining, for example, an anticipated length of the medical device needed to enter the patient P at the insertion site and traverse the patient vasculature for disposition at the target placement position. For instance, a patient's height and weight may be used to ensure the anticipated length is consistent with the patient's height. As one illustrative example in which the insertion site S is located on the patient's arm, a patient's height may correspond to a particular arm length, such as an average arm length derived from a historical database of patient measurements. The logic 120 may perform a comparison between the anticipated length of the medical device as derived from the positional-tracking data and the average arm length corresponding to the patient height. The comparison may provide an indication as to whether the anticipated length is within a threshold distance of the average arm length corresponding to the patient height, which enables the logic 120 to confirm the anticipated length is likely correct. In other situations, various patient measurements (e.g., arm circumference) may assist in determining depth of a target vessel. In some instances, the use of a patient's gender, ethnicity and/or age may be used to extrapolate expected measurements corresponding to an anticipated length of a medical device needed to enter the patient P at the insertion site and traverse the patient vasculature for disposition at the target placement position, a recommended trim length of the medical device, recommended device configurations, etc. In some instances, the extrapolated measurements may be utilized by the system to alter the determined anticipated length, recommended trim length, and/or recommended device configurations. In one illustrative example, based on a patient being a Hispanic 55-year-old female, the extrapolation of this data may indicate that the recommended trim length should be shortened by 5%.

In some embodiments, the console 102 may receive user input via a peripheral device 1208 (e.g., a keyboard) corresponding to certain patient specific data 1202, which is displayed via a graphical user interface 1200 on the display 104. The peripheral device 1208 may be connected to the console 102 via a wired or wireless connection (collectively illustrated as connection 1210). In other embodiments, the console 102 may obtain the patient specific data by querying a database such as a patient records database 1204. In some instances, the patient records database 1204 may be a component of the console 102 (e.g., stored on non-transitory computer-readable medium of the console 102) or accessible by the console 102 (e.g., stored on cloud computing resources). The console 102 may access the patient records database 1204 via a communicative coupling 1206 (e.g., via queries sent over a network such as a local area network (LAN) and/or the internet).

Figure 13:
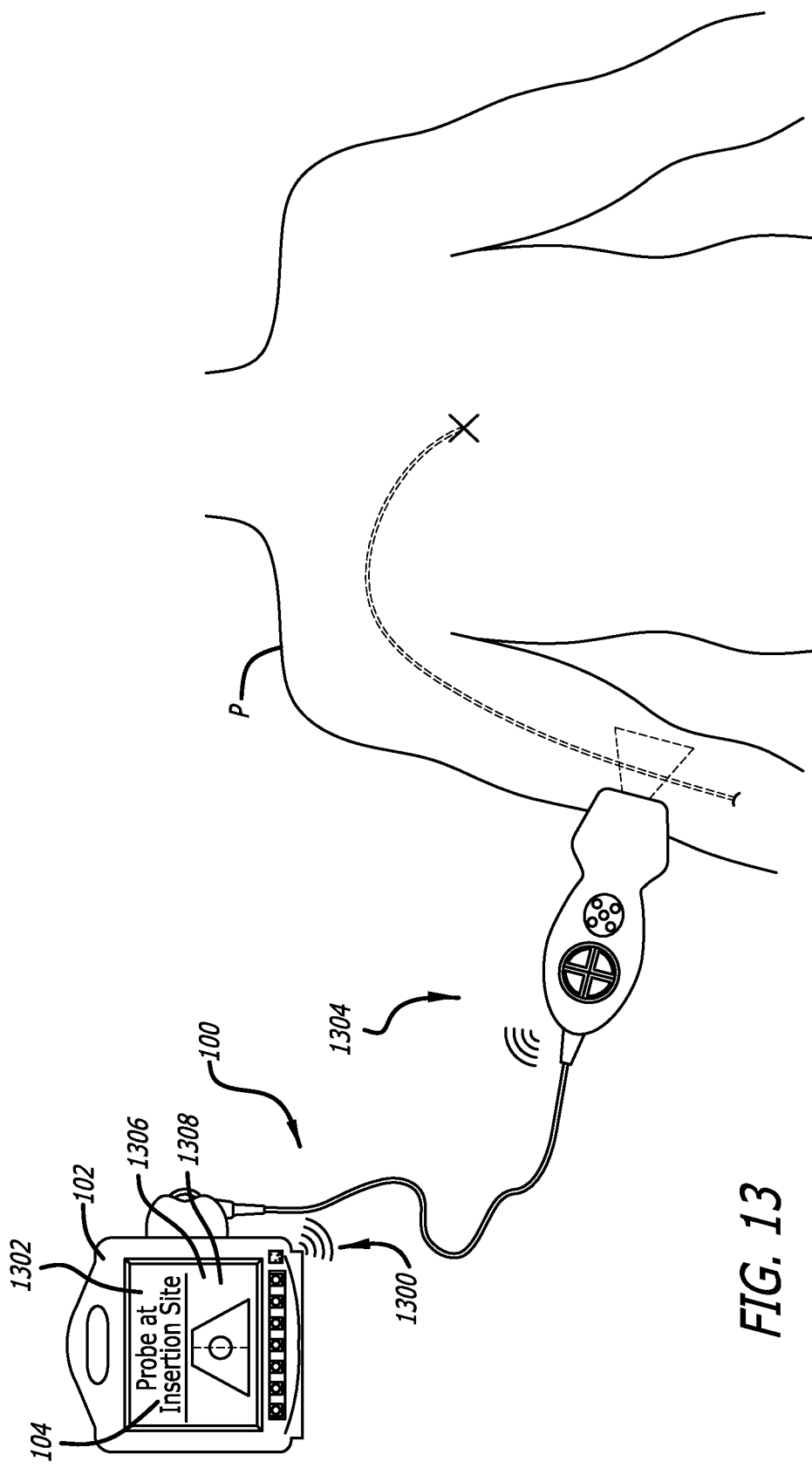
FIG. 13 illustrates feedback provided to a user upon positioning of an ultrasound probe to a starting point of the mapping procedure of the implementation displayed in FIGS. 9-10 in accordance with some embodiments.

Referring to FIG. 13, feedback provided to a user upon positioning of an ultrasound probe to a starting point of the mapping procedure of the implementation displayed in FIGS. 9-10 is shown in accordance with some embodiments. The illustration of FIG. 13 provides multiple discussion points regarding feedback provided to a user upon positioning of an ultrasound probe to a starting point of the mapping procedure of the implementation displayed in FIGS. 9-10 (e.g., tracking the insertion pathway). In many situations, following the mapping procedure discussed above, the probe 106 may be removed from the insertion site S, which is then cleaned and dressed for insertion of a needle and/or other medical device (e.g., the insertion site S and surrounding area is sterilized, and draping may be placed on portions of the patient P. The feedback is intended to indicate when the probe 106 has been placed at the starting point following the sterilization of the insertion site S such that the positioning and orientation of the probe 106 post-sterilization corresponds to the positioning and orientation of the probe 106 pre-sterilization (i.e., during the mapping procedure).

For example, embodiments seek to provide methodologies that ensure the vasculature (and location thereof) identified during the mapping procedure (also referred to as a "pre-scan procedure") is returned to during access/device insertion. During the mapping procedure, the ultrasound probe is used to identify a preferred location for access into the vasculature and to track an insertion pathway. Subsequently, the probe is removed, and the procedure space is prepared. After preparing the procedure space, it is intended that the clinician is able to place the probe 106 back at the same location and identify the same vessel as indicated/utilized in the mapping procedure. Specifically, the analyses performed, and results obtained from the mapping procedure are specific to the starting position (and possibly the orientation). Thus, if the clinician returns the probe 106 to a slightly modified location, many of the analyses and results based on the anatomy may no longer be valid.

Audible feedback 1300 may be one type of feedback provided to a clinician from, for example a speaker included in the console 102. For instance, an audible queue that the probe 106 has been returned to the starting position (e.g., the starting position 900 of FIG. 9) may be provided. Additionally, visual feedback 1302 may be provided on the display 104, which may include a graphical indicator (e.g., change of color of the screen or a portion of the screen) or the rendering of text (e.g., "probe at insertion site"). Another example of feedback may include haptic feedback 1304 provided by the probe 106 (or by another device communicatively coupled to the console 102 such as a wearable, e.g., a smart watch). As yet another example of feedback, the display 104 may display a graphic in which an original ultrasound image 1306 is displayed (taken during the mapping procedure at the starting position) and a current ultrasound image 1308 displayed as an overlay such that the clinician may visualize movement of the probe 106 toward the starting position with respect to the ultrasound images (i.e., the ultrasound images 1306, 1308 will match when the probe 106 returns to the starting position). It should be understood that multiple types of feedback may be provided in a single embodiment.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. An ultrasound-imaging system, comprising:
an ultrasound probe including an array of ultrasonic transducers, wherein activated ultrasonic transducers of the array of ultrasonic transducers are configured to emit generated ultrasound signals into a patient, receive reflected ultrasound signals from the patient, and convert the reflected ultrasound signals into corresponding electrical signals for processing into an ultrasound image, wherein the ultrasound probe is configured to obtain positional-tracking data as the ultrasound probe is moved externally along a patient body from a starting position to an end position; and
a console configured to communicate with the ultrasound probe, the console including one or more processors and a non-transitory computer-readable medium having stored thereon logic, when executed by the one or more processors, causes operations including:
receiving and processing the corresponding electrical signals to generate the ultrasound image,
receiving the positional-tracking data,
determining metrics of a path traveled by the ultrasound probe, wherein the metrics of the path traveled by the ultrasound probe include a distance traveled from the starting position to the end position,
generating a graphical representation of the patient body including one or more vessels based on the positional-tracking data;
receiving user input selecting one or more vessels comprising an insertion pathway; and
providing insertion recommendations including a trim length of a medical device to be inserted into the patient based on the metrics of the path traveled by the ultrasound probe and the user input selecting the one or more vessels.

2. The ultrasound-imaging system of claim 1, wherein obtaining the positional-tracking data is a pre-scan procedure performed prior to sanitizing an insertion site.

3. The ultrasound-imaging system of claim 1, wherein the ultrasound probe is configured to obtain the positional-tracking data by way of an inertial measurement unit that is comprised of one or more of an accelerometer, a gyroscope, and a magnetometer.

4. The ultrasound-imaging system of claim 1, wherein the ultrasound probe is configured to obtain the positional-tracking data by way of a multi-core optical fiber that is configured in a predetermined geometry within the ultrasound probe.

5. The ultrasound-imaging system of claim 1, wherein the ultrasound probe is configured to obtain the positional-tracking data by way of a magnetic sensor, and the ultrasound-imaging system further comprises one or more magnetic targets, wherein the magnetic sensor is configured to detect variations in a strength of magnetic fields generated by the one or more magnetic targets as the ultrasound probe moves from the starting position to the end position.

6. The ultrasound-imaging system of claim 1, further comprising an alternative reality device communicatively coupled to the console and configured to display an alternative reality display of the ultrasound image as the ultrasound probe moves from the starting position to the end position.

7. The ultrasound-imaging system of claim 2, wherein at least one of the console or the ultrasound probe are configured to provide feedback when the ultrasound probe is returned to the starting position following sanitizing the insertion site.

8. The ultrasound-imaging system of claim 7, wherein the feedback is any of audible feedback, haptic feedback, or visual feedback.

9. The ultrasound-imaging system of claim 1, wherein the logic, when executed by the one or more processors, causes further operations including receiving user input providing refinement data corresponding to an aspect of the positional-tracking data or the ultrasound image, wherein the refinement data includes any of a depth of an imaged vessel with the ultrasound image or patient specific information.

10. A non-transitory computer-readable medium having stored thereon instructions that, when executed by one or more processors, cause the one or more processors to perform operations including:

receiving and processing electrical signals to generate an ultrasound image, wherein the electrical signals are received from an ultrasound probe including an array of ultrasonic transducers, wherein activated ultrasonic transducers of the array of ultrasonic transducers are configured to emit generated ultrasound signals into a patient, receive reflected ultrasound signals from the patient, and convert the reflected ultrasound signals into corresponding electrical signals for processing into the ultrasound image, wherein the ultrasound probe is configured to obtain positional-tracking data as the ultrasound probe is moved externally along a patient body from a starting position to an end position;

receiving and processing the electrical signals to generate the ultrasound image, receiving the positional-tracking data, determining metrics of a path traveled by the ultrasound probe, wherein the metrics of the path traveled by the ultrasound probe include a distance traveled from the starting position to the end position, generating of a graphical representation of the patient body including one or more vessels based on the positional-tracking data;

receiving user input selecting one or more vessels comprising an insertion pathway; and providing insertion recommendations including a trim length of a medical device to be inserted into the patient based on the metrics of the path traveled by the ultrasound probe and the user input selecting the one or more vessels.

11. The non-transitory computer-readable medium of claim 10, wherein obtaining the positional-tracking data is a pre-scan procedure performed prior to sanitizing an insertion site.

12. The non-transitory computer-readable medium of claim 10, wherein the ultrasound probe is configured to obtain the positional-tracking data by way of an inertial measurement unit that is comprised of one or more of an accelerometer, a gyroscope, and a magnetometer.

13. The non-transitory computer-readable medium of claim 10, wherein the ultrasound probe is configured to obtain the positional-tracking data by way of a multi-core optical fiber that is configured in a predetermined geometry within the ultrasound probe.

14. The non-transitory computer-readable medium of claim 10, wherein the ultrasound probe is configured to obtain the positional-tracking data by way of a magnetic sensor that is configured to detect variations in a strength of magnetic fields generated by one or more magnetic targets as the ultrasound probe moves from the starting position to the end position.

15. The non-transitory computer-readable medium of claim 10, wherein the instructions that, when executed by the one or more processors, causes the one or more processors to perform further operations including:

generating an alternative reality display of the ultrasound image as the ultrasound probe moves from the starting position to the end position configured for rendering by an alternative reality device.

16. The non-transitory computer-readable medium of claim 11, wherein the instructions that, when executed by the one or more processors, cause the one or more processors to perform further operations including:

generating feedback when the ultrasound probe is returned to the starting position following sanitizing the insertion site.

17. The non-transitory computer-readable medium of claim 16, wherein the feedback is any of audible feedback, haptic feedback, or visual feedback.

18. The non-transitory computer-readable medium of claim 10, wherein the instructions that, when executed by the one or more processors, causes the one or more processors to perform further operations including receiving user input providing refinement data corresponding to an aspect of the positional-tracking data or the ultrasound image, wherein the refinement data includes any of a depth of an imaged vessel with the ultrasound image or patient specific information.

\* \* \* \* \*